(12) United States Patent
Pluta et al.

(10) Patent No.: US 9,804,112 B2
(45) Date of Patent: Oct. 31, 2017

(54) SELECTIVE CHARACTERIZATION OF MATERIAL UNDER TEST (MUT) WITH ELECTROMAGNETIC IMPEDANCE TOMOGRAPHY AND SPECTROSCOPY

(71) Applicant: TransTech Systems, Inc., Schenectady, NY (US)

(72) Inventors: Sarah E. Pluta, Scotia, NY (US); Donald D. Colosimo, Saratoga Spring, NY (US); John W. Hewitt, Niskayuna, NY (US)

(73) Assignee: TransTech Systems, Inc., Schenectady, NY (US)

( * ) Notice: Subject to any disclaimer, the term of this patent is extended or adjusted under 35 U.S.C. 154(b) by 401 days.

(21) Appl. No.: 14/547,602

(22) Filed: Nov. 19, 2014

(65) Prior Publication Data
US 2015/0137831 A1    May 21, 2015

Related U.S. Application Data

(60) Provisional application No. 61/906,664, filed on Nov. 20, 2013.

(51) Int. Cl.
*G01R 27/02*    (2006.01)
*G01V 3/08*    (2006.01)
(Continued)

(52) U.S. Cl.
CPC ......... *G01N 27/026* (2013.01); *A61B 5/0478* (2013.01); *A61B 5/0536* (2013.01);
(Continued)

(58) Field of Classification Search
CPC ...... G01N 27/00; G01N 27/02; G01N 27/026; G01N 22/00; G01N 22/02; G01N 22/04; G01D 5/24; G01D 5/241; G01D 5/2412; G01D 5/2417; G01R 27/00; G01R 27/02; G01R 27/26; G01R 27/2605; G01R 33/00; G01R 33/20; G01R 33/24; G01R 33/32; G01R 33/323; G01R 33/44; G01R 33/48;
(Continued)

(56) References Cited

U.S. PATENT DOCUMENTS 4,484,476 A * 11/1984 Nagasaki ............... G01H 3/125
                                                        73/606
5,900,736 A    5/1999 Sovik et al.
(Continued)

OTHER PUBLICATIONS

U.S. Appl. No. 14/027,520, filed Sep. 16, 2013.

*Primary Examiner* — Hoai-An D Nguyen
(74) *Attorney, Agent, or Firm* — Hoffman Warnick LLC

(57) ABSTRACT

A method of extracting complex impedance from selected volumes of the material under test (MUT) combined with various embodiments of electrode sensor arrays. Configurations of linear and planar electrode arrays provide measured data of complex impedance of selected volumes, or voxels, of the MUT, which then can be used to extract the impedance of selected sub-volumes or sub-voxels of the MUT through application of circuit theory. The complex impedance characteristics of the sub-voxels may be used to identify variations in the properties of the various sub-voxels of the MUT, or be correlated to physical properties of the MUT using electromagnetic impedance tomography and/or spectroscopy.

18 Claims, 22 Drawing Sheets

(51) Int. Cl.
*A61B 5/04* (2006.01)
*G01N 27/02* (2006.01)
*A61B 5/053* (2006.01)
*G01R 33/32* (2006.01)
*A61B 5/0478* (2006.01)
*G01N 22/04* (2006.01)
*G01N 22/02* (2006.01)

(52) U.S. Cl.
CPC ........... *G01R 27/02* (2013.01); *G01R 33/323* (2013.01); *G01V 3/08* (2013.01); *G01N 22/02* (2013.01); *G01N 22/04* (2013.01)

(58) Field of Classification Search
CPC ......... G01R 33/4808; A61B 5/00; A61B 5/04; A61B 5/0476; A61B 5/0478; A61B 5/05; A61B 5/053; A61B 5/0536; A61B 5/055; A61N 1/00; A61N 1/02; A61N 1/04; A61N 1/0404; A61N 1/0408; A61N 1/0456; A61N 1/18; A61N 1/32; A61N 1/36; A61N 1/36014; G01V 3/00; G01V 3/08; G01V 3/12; G01V 3/38
USPC ....... 324/600, 629, 647, 658–665, 667, 669, 324/671, 672, 684, 686, 689, 500, 512, 324/527, 532, 533, 534, 637, 638, 642, 324/646, 323, 326, 327; 702/47, 52; 600/300, 372
See application file for complete search history.

(56) References Cited

U.S. PATENT DOCUMENTS

| | | | |
|---|---|---|---|
| 6,400,161 B1 | 6/2002 | Geisel | |
| 6,414,497 B1 | 7/2002 | Sovik et al. | |
| 6,501,984 B1* | 12/2002 | Church | A61B 5/0536 600/547 |
| 6,677,763 B2 | 1/2004 | Geisel | |
| 7,219,021 B2 | 5/2007 | Liu et al. | |
| 9,326,699 B2* | 5/2016 | Tucker | A61B 5/0476 |
| 2002/0173041 A1* | 11/2002 | Canas | G01N 33/12 436/21 |
| 2004/0242989 A1* | 12/2004 | Zhu | A61B 5/0536 600/407 |
| 2006/0004301 A1* | 1/2006 | Kasevich | A61B 5/0536 600/547 |
| 2009/0084674 A1* | 4/2009 | Holzhacker | A61B 5/0536 204/286.1 |
| 2013/0307564 A1 | 11/2013 | Colosimo et al. | |
| 2015/0002168 A1* | 1/2015 | Kao | A61B 5/0536 324/600 |
| 2015/0025353 A1* | 1/2015 | Salonius | A61B 5/0537 600/388 |
| 2016/0161624 A1* | 6/2016 | Pluta | G01V 3/12 324/327 |

* cited by examiner

Electrode Shapes

Rectangular with rounded corners

Ellipsoid

Circular

SELECTIVE CHARACTERIZATION OF MATERIAL UNDER TEST (MUT) WITH ELECTROMAGNETIC IMPEDANCE TOMOGRAPHY AND SPECTROSCOPY

CROSS-REFERENCE TO RELATED APPLICATIONS

This application claims priority to U.S. Provisional Patent Application No. 61/906,664, which is hereby incorporated by reference in its entirety.

TECHNICAL FIELD

The invention relates to securing impedance tomographic and spectrographic characterizations of specific volumes of a material under test and the design of various types of apparatuses consisting of sensor arrays for use with electromagnetic impedance tomographic and spectrographic measurement devices to secure the data for the application of the disclosed method. The design of the sensor array is such that data is secured in a fashion to permit the tomographic detection of selected volumes of the material under test at varying depths and locations and the spectrographic characterization of the electromagnetic properties of the material within that volume which may then be related to a physical attribute of the material under test.

BACKGROUND

The use of electromagnetic tomographic and spectrographic measurement devices have been identified in U.S. Provisional Patent Application Nos. 61/647,848 and 61/703,488 (each of which is hereby incorporated by reference in its entirety) to locate specified volumes within a material under test and to characterize that volume based upon its electromagnetic characteristics. In order to accomplish this with an instrument that may be readily used in a clinical or field environment requires the combination of apparatus, systems, methods and programs as disclosed in the filings noted above. However, once the basic approaches are disclosed, other applications may be identified and implemented based primarily on changes in the design of the electrode array combined with the previously disclosed art. The ability to change the application or improve on previously disclosed applications also provides the ability to secure data such that the electromagnetic characteristics of specific computational volumes may be readily determined from the electromagnetic properties of measured volumes.

The method to determine the tomographic and spectrographic information for specific volumes of the material under test (MUT) is based on using an equivalent circuit model of the actual measurements made to characterize the impedance characteristics of various sub-volumes of the measured volumes combined with the impedance characteristics of other measured volumes as described below.

The apparatus consisting of the electrode arrangement in the sensor array allows securing of the data for the computation of the electromagnetic characteristic of a volume within the material under test which may then be related to some physical parameter of the MUT. The number of electrodes in the sensor array is related to the number of layers of the MUT to be characterized and the number of volumes of the MUT to be measured. The number of measured volumes is related to the number of computed volumes since the computed volume is a sub-volume of the larger measured volumes. The only measured volume of interest that is identical to the computed value is the smallest measured volume closest to the sensor array. This volume may consist of a volume of the MUT, a combination of the MUT and air, or all air. The composition of the volume depends on whether the sensor array is in contact with the MUT or standing off from the MUT. So as the number of layers of interest of the MUT to be investigated increases, the number of the electrodes in the sensor array increases.

In order to apply the method to secure the measured volume data, various designs and measuring strategies are required to obtain accurate data and secure them in an efficient and timely manner. The method and the apparatus comprising these designs and approaches are the subject of the disclosed invention.

SUMMARY OF THE INVENTION

Aspects of the invention include methods, apparatus, and systems to secure the electromagnetic impedance characteristics of selected volumes of materials under test.

Embodiments include the method with apparatus consisting of various electrode sensor arrays incorporated into systems configured to communicate with various materials under test. The system(s) can include: a signal generator operably connected with the array of electrodes, the signal generator for transmitting oscillating electromagnetic field signals through the array of electrodes at a range of selected frequencies; a signal detector operatively connected to the array of electrodes, the array of electrodes in communication with the material under test; a signal comparator operatively connected to the signal generator and the signal detector; and at least one computing device operably connected with the signal comparator. The at least one computing device is configured to determine the electromagnetic impedance characteristics of selected volumes of the MUT. The at least one computing device may also be configured to correlate the electromagnetic impedance characteristics of selected volumes of the MUT to physical properties of those volumes. The at least one computing device may also provide output to the user in various formats and transfer data files to another computer by various means.

The method and the various embodiments of the electrode sensor arrays presented in this disclosure provide improvements over conventional approaches by securing electromagnetic impedance spectrographic and tomographic characteristics of selected volumes of the MUT which may then correlate the impedance characteristics to physical properties of the selected volumes of the MUT.

Additionally, the various embodiments of the electrode sensor arrays presented in this disclosure provide improvements over conventional approaches by securing electromagnetic impedance spectrographic and tomographic characteristics of selected volumes of the MUT which may then correlate the impedance characteristics with anomalies within the selected volumes of the MUT.

According to various embodiments shown and described herein, electromagnetic impedance spectrographic and tomographic characteristics of selected volumes of the MUT can be obtained by forming electrically conductive communication (contacting) between a sensor array (e.g., linear sensor array, or set of linear sensor arrays forming a planar sensor array) and the MUT; or by non-electrically conductive communication (non-contacting) with the MUT.

A first aspect includes a method of characterizing select volumes of a material under test (MUT) using electromagnetic impedance tomography and spectroscopy, the method including: obtaining the complex impedance over a range of frequencies of volumes or voxels of the MUT with a linear or a planar array of electrodes in communication with the MUT; and applying series and parallel circuit theory to compute the complex impedance at each frequency of segments of the measured volumes or sub-voxels using the measured values of the voxels.

A second aspect includes a system including: an array of electrodes for communicating with a surface and a subsurface beneath the surface; a signal generator operably connected with the array of electrodes; and at least one computing device operably connected with the signal generator and the array of electrodes, the at least one computing device configured to: instruct the signal generator to transmit a first set of tomographic signals (e.g., at a selected frequency) from a first subset of the array of electrodes into the surface and the subsurface; obtain a first return signal from the array of electrodes after the transmitting of the first set of tomographic signals; instruct the signal generator to transmit a second set of tomographic signals (e.g., at the selected frequency) from a second subset of the array of electrodes into the surface and the subsurface based upon the first return signal, the second subset of the array of electrodes including at least one electrode not included in the first subset of the array of electrodes; obtain a second return signal from the array of electrodes after the transmitting of the second set of tomographic signals; and combine the first return signal and the second return signal to determine a characteristic of at least one of the surface or the subsurface.

A third aspect includes a method of characterizing select volumes of a material under test (MUT) using an array of electrodes, the method including: instructing a signal generator to transmit a first set of tomographic signals (e.g., at a selected frequency) from a first subset of the array of electrodes into the MUT; obtaining a first return signal from the array of electrodes after the transmitting of the first set of tomographic signals; instructing the signal generator to transmit a second set of tomographic signals (e.g., at the selected frequency) from a second subset of the array of electrodes into the MUT based upon the first return signal, the second subset of the array of electrodes including at least one electrode not included in the first subset of the array of electrodes; obtaining a second return signal from the array of electrodes after the transmitting of the second set of tomographic signals; and combining the first return signal and the second return signal to determine a characteristic of the MUT.

A fourth aspect includes a computer program product having program code stored on a computer readable storage medium, which when executed by at least one computing device coupled to a signal generator and an array of electrodes, causes the at least one computing device to execute a method of characterizing a select volume of a material under test (MUT) by performing actions including: instructing the signal generator to transmit a first set of tomographic signals (e.g., at a selected frequency) from a first subset of the array of electrodes into the MUT; obtaining a first return signal from the array of electrodes after the transmitting of the first set of tomographic signals; instructing the signal generator to transmit a second set of tomographic signals (e.g., at the selected frequency) from a second subset of the array of electrodes into the MUT based upon the first return signal, the second subset of the array of electrodes including at least one electrode not included in the first subset of the array of electrodes; obtaining a second return signal from the array of electrodes after the transmitting of the second set of tomographic signals; and combining the first return signal and the second return signal to determine a characteristic of the select volume of the MUT.

DETAILED DESCRIPTION

Figure 1:
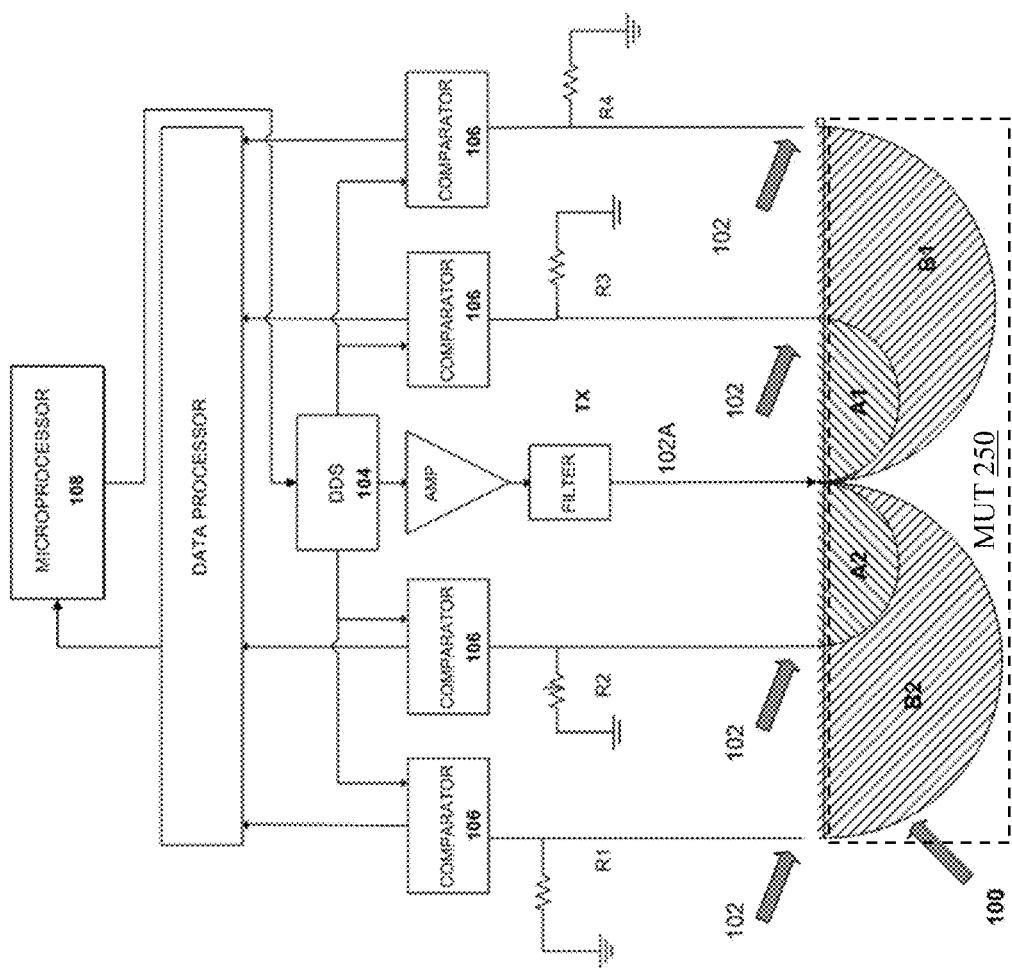
FIG. 1 is an illustration of a five electrode linear array with variable functions and showing the measured volumes of the MUT.

The following discussion expands on and improves the methodology disclosed in prior art to convert the measured impedance in volumes into the calculated impedance in sub-volumes. This methodology is termed Volume Differentiation and Removal (VDR). The term "voxel" will be used to refer to "volume pixels", which is the volume of the material under test (MUT) in which the impedance is directly measure. The term "sub-voxel" is used to denote the sub-volume of the MUT in which the impedance is computed from the measured values of impedance in the voxel.

According to various embodiments, an MUT can include any material capable of being characterized via one or more approaches shown and/or described herein. In various embodiments, an MUT includes an organic material such as a soil, or a biological material such as tissue, sub-tissue, organs, fluids, etc. An MUT can include synthetic, composite and/or other blended/modified materials. An MUT can also include elemental materials, as well as materials including impurities. It is understood that the teachings described according to the various embodiments herein can be applied to any MUT described herein, as well as other materials that can be characterized according to the approaches of the various embodiments.

In the following description, reference is made to the accompanying drawings that form a part thereof, and in which is shown by way of illustration specific exemplary embodiments in which the present teachings may be practiced. These embodiments are described in sufficient detail to enable those skilled in the art to practice the present teachings and it is to be understood that other embodiments may be utilized and that changes may be made without departing from the scope of the present teachings. The following description is, therefore, merely exemplary.

Illustrations with respect to one or more implementations, alterations and/or modifications can be made to the illustrated examples without departing from the spirit and scope of the appended claims. In addition, while a particular feature may have been disclosed with respect to only one of several implementations, such feature may be combined with one or more other features of the other implementations as may be desired and advantageous for any given or particular function. Furthermore, to the extent that the terms "including", "includes", "having", "has", "with", or variants thereof are used in either the detailed description and the claims, such terms are intended to be inclusive in a manner similar to the term "comprising." The term "at least one of" is used to mean one or more of the listed items can be selected.

Notwithstanding that the numerical ranges and parameters setting forth the broad scope of embodiments are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as "less than 10" can assume negative values, e.g., −1, −2, −3, −10, −20, −30, etc.

U.S. Pat. Nos. 5,900,736; 6,400,161; 6,414,497; and 6,677,763 (each of which is hereby incorporated by reference in its entirety) presents a two electrode sensor array as a means to evaluate the density of asphalt using electromagnetic impedance characteristics of the asphalt. This concentric two or three electrode sensor may also be classified electrically as a coplanar wave guide. This prior art does not use any spectrographic or tomographic approaches but illustrates two electrode geometries for use with electromagnetic impedance measuring devices. U.S. Pat. No. 7,219,021 (hereby incorporated by reference in its entirety) presents the use of electromagnetic impedance spectroscopy to evaluate the density and moisture of soils with an electrode geometry similar to that in U.S. Pat. Nos. 5,900,736 and 6,414,497. These electrode arrays are in non-conductive communication with the MUT. U.S. Provisional Patent Application Nos. 61/647,848 and 61/703,488 (each of which is hereby incorporated by reference in its entirety) present two different methods of evaluating a MUT with impedance spectroscopy and impedance tomography with linear electrode arrays in non-conductive communication the MUT.

The method and the various embodiments of the electrode sensor arrays presented in this disclosure provide various improvements to U.S. Provisional Patent Application Nos. 61/647,848 and 61/703,488, to secure electromagnetic impedance spectrographic and tomographic characteristics of selected volumes of the MUT which may then correlate the impedance characteristics to physical properties of the selected volumes of the MUT.

Additionally, the various embodiments of the electrode sensor arrays presented in this disclosure provide various improvements to U.S. Patent Application Nos. 61/647,848 and 61/703,488 to secure electromagnetic impedance spectrographic and tomographic characteristics of selected volumes of the MUT which may then correlate the impedance characteristics with anomalies within the selected volumes of the MUT.

As described in U.S. Provisional Patent Application No. 61/703,488, a schematic depiction of an impedance measuring system is shown in FIG. 1. This schematic depiction shows an impedance sensor system 100 with five electrodes 102, one of which, 102A, provides the input of the signal over a range of frequencies supplied by a signal generator 104, e.g., a DDS (Direct Digital Synthesizer). In this example, the other four electrodes can complete the circuit with the signal passing through the MUT 250. The original signal from the signal generator 104 (DDS) can be compared to the signals passing through the MUT 250. The output of the comparator 106 is the difference in the magnitude and the phase shift from the original signal to the return signal. This magnitude and phase data of the transmitted and the return signals can be communicated to the microprocessor 108 which processes the data and transmits it to a statistical process control (e.g., an embedded component in the microprocessor 108). The microprocessor 108 can also control the DDS 104 to select the frequencies to be generated. In the embodiment shown, the order of the transmitting electrode and the receiving electrodes are fixed.

In this example shown in FIG. 1, the electrodes 102 are configured to communicate with the MUT 250, but are not in electrical contact with the MUT 250, that is, they are electrically isolated from the MUT 250 (e.g., by an insulating material or an air gap). In some cases, the minimum number of electrodes in the array is two (2): a transmitting electrode and a receiving electrode. However, in other applications, the array may consist of a one-dimensional array or a two-dimensional array of multiple electrodes, e.g., 5 or more electrodes, with the electrodes operating in subsets of one transmitting electrode and one or more receiving electrodes.

In this example, the impedance characteristics of four voxels of the MUT 250 can be measured. As noted herein, a voxel is fraction of a three-dimensional space, that is, a volumetric pixel or volume element that represents a value on a regular grid in three-dimensional space. In some cases, a voxel is known as a three-dimensional equivalent of a pixel (two-dimensional element). The difference between the power of the transmitted signal and the signal passing through the MUT 250 is defined as the magnitude, m. The shift in phase between the transmitted signal and the signal passing through the MUT 250 is the phase angle, ϕ. These are measured by the comparators, 106, in FIG. 1. These are the measured quantities for the voxels A1, A2, B1 and B2.

In the discussion of the measurements and interpreting aspects of the complex impedance, it may be beneficial to define terms that may be calculated from the output of an electromagnetic measurement device which are the magnitude of the power difference between the transmitted signal and the signal that is transmitted through the MUT, m, and the phase angle, $\phi$, shift between the transmitted signal and the signal transmitted through the MUT. Impedance (Z) is represented mathematically as a complex relation consisting of a real part, resistance, and an imaginary part, reactance:

$$Z=R+iX;$$

Z=the complex value of Impedance;
R=m*cos $\phi$; the Resistance;
X=m*sin $\phi$; the Reactance;
Resistance, R, is a material's opposition to the flow of electric current;
Reactance, X, is a material's opposition to alternating current due to capacitance (capacitive reactance) and/or inductance (inductive reactance);
Admittance (Y) is a complex quantity which is the inverse of Impedance, and results in the definition of the terms of Conductance and Susceptance:

$$Y=1/Z=G+iB;$$

Susceptance (B) is a complementary representation of the reactance in the term admittance and is defined mathematically as:

$$B=-X/(R^2+X^2);$$

The Susceptance may be computed from the measured properties as follows:

$$B=\text{the Susceptance}=-\sin \phi/m;$$

The Conductance (G) may be computed from the measured properties as follows:

$$G=\text{the Conductance}=\cos \phi/m.$$

In the description of the various embodiments, the value of the impedance, Z, will be used in the various equations and relations pertaining to the measurements made of the voxels in the MUT (e.g., MUT 250) and the computation of the sub-voxels. However, a value of the resistance, reactance, admittance, conductance, or susceptance may replace impedance in any of the examples below.

It should be noted that for a tomographic solution only data at one frequency is required. However, for the use of a spectrographic analysis to characterize a property of the MUT, computations over a range of frequencies are required. That is, the above equations are applied to data from each frequency to obtain the impedance data over the range of frequencies. These data are then applied to the Volume Differentiation and Removal methodology as described below.

Figure 2:
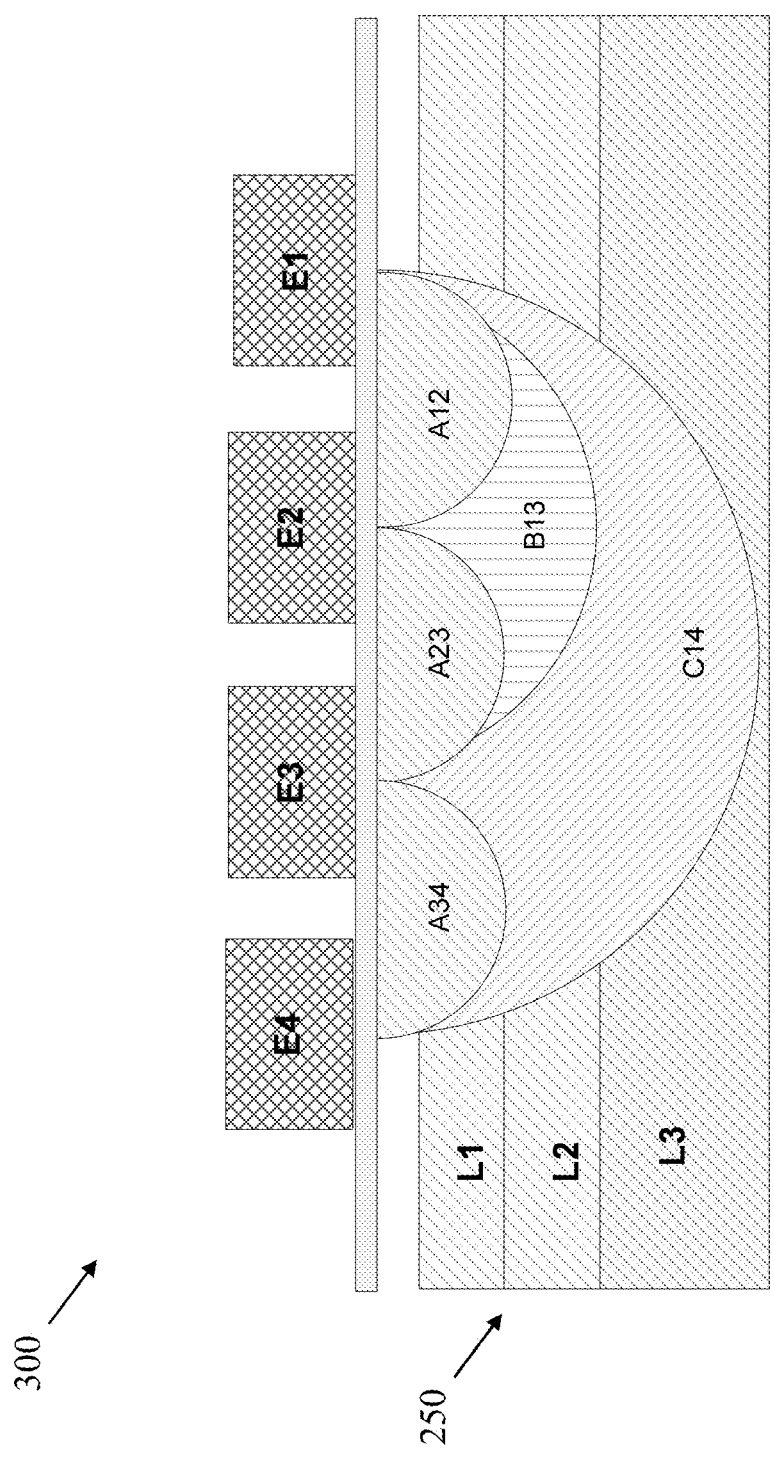
FIG. 2 is an illustration of the use of a four electrode array to measure different volumes of the MUT.
Figure 3:
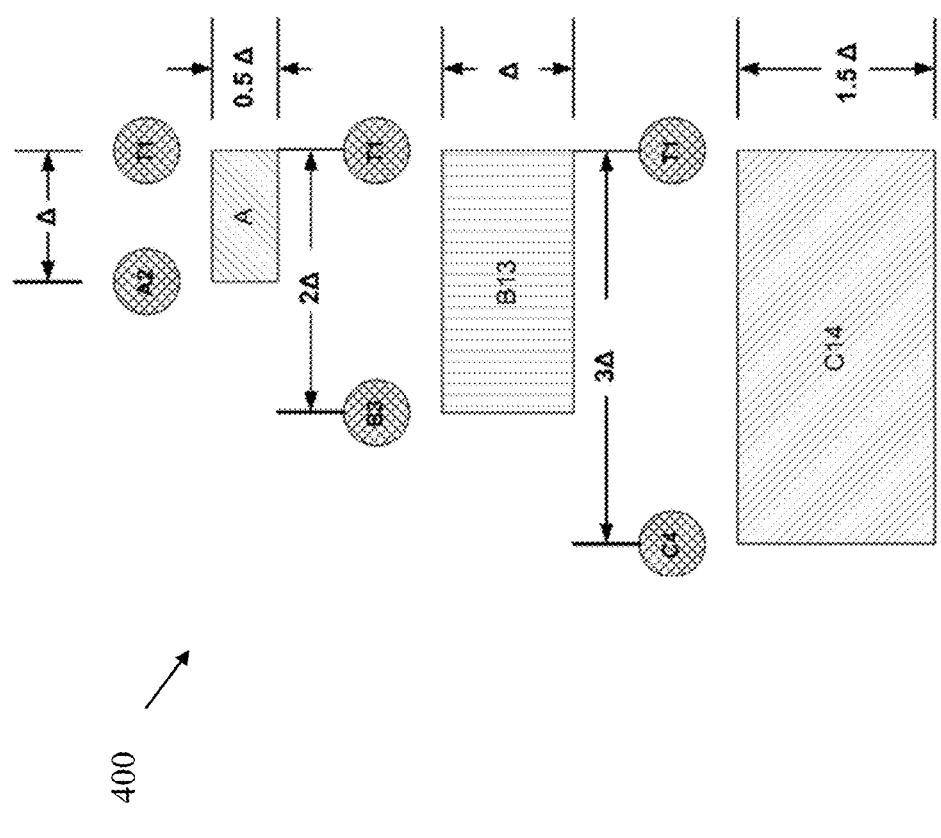
FIG. 3 is an illustration of the different measured volumes.
Figure 4:
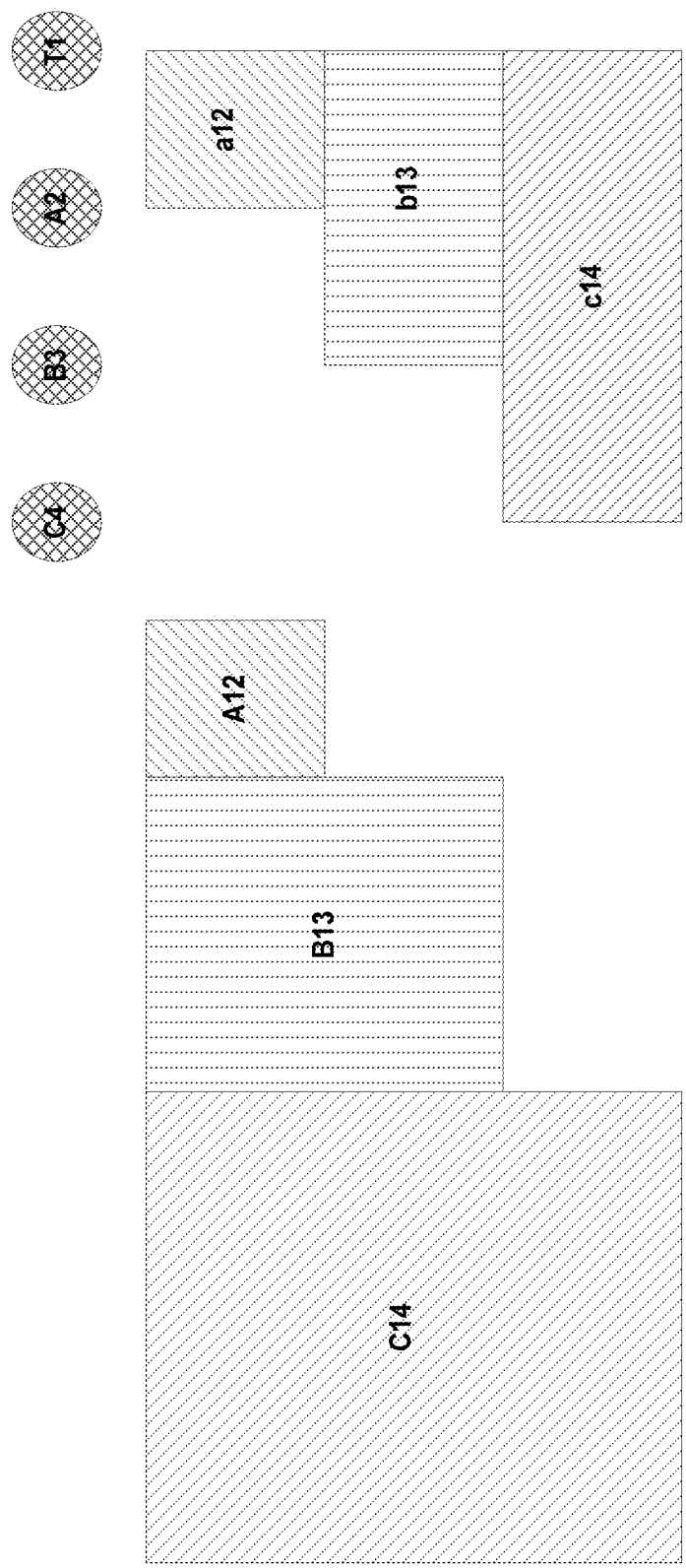
FIG. 4 is an illustration of the relation of the measured volumes to the computed volumes.
Figure 5:
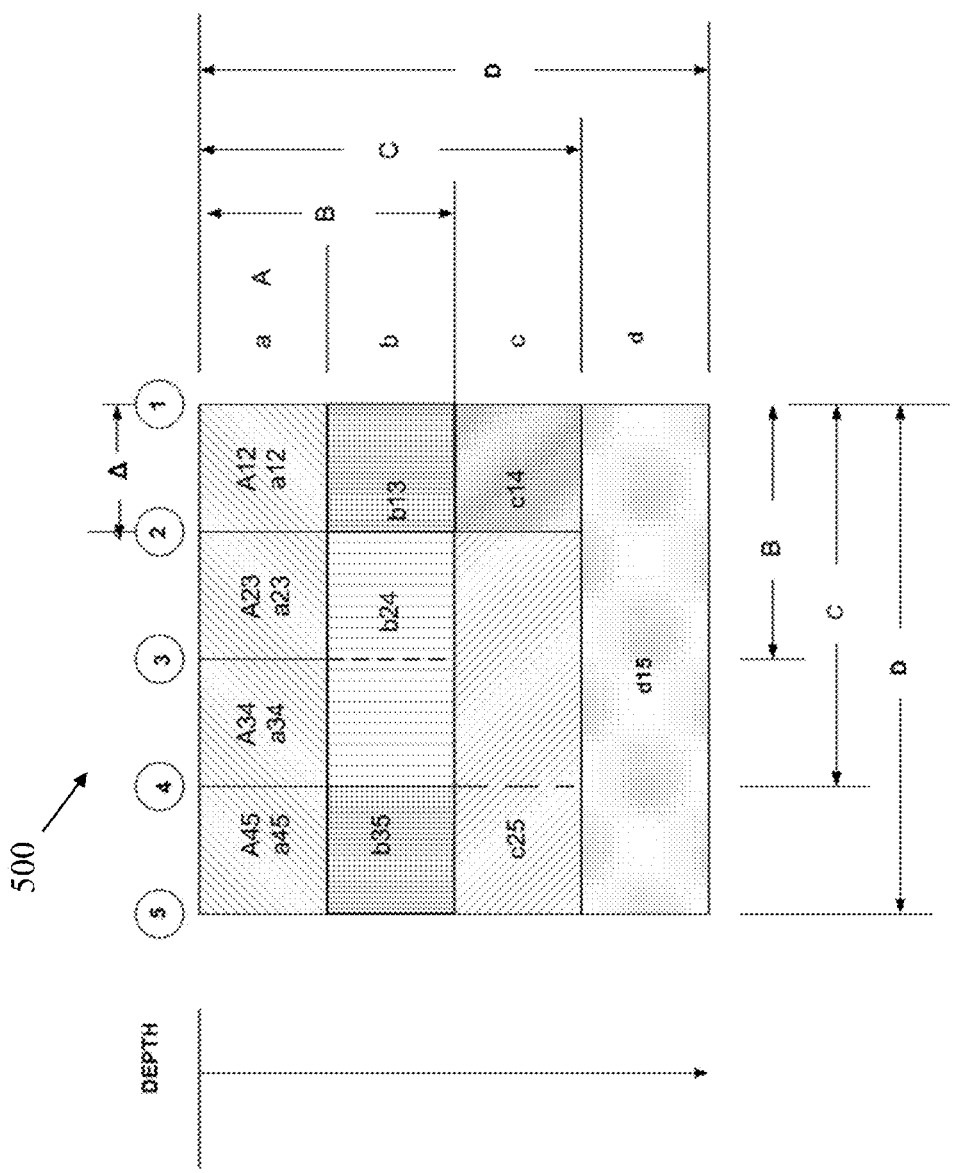
FIG. 5 is an illustration of the relation of and the nomenclature for the computed volumes.

The general approach to the Volume Differentiation and Removal (VDR) methodology illustrates various beneficial features of the methods and of the various arrays disclosed herein. In the following discussions, a capital letter refers to the measured voxel and a lower case letter refers to the sub-voxel (a portion of a voxel, where a compilation of all sub-voxels form a whole voxel). Numbers following the voxel or sub-voxel denote the numbered electrodes which generate/receive the signal(s) passing through the MUT (e.g., MUT 250). Referring to FIG. 2, an example four electrode linear sensor array 300 is illustrated, wherein each electrode E 1, E 2, E 3, E 4 may either be a transmitting or a receiving electrode, for transmitting or receiving a set of tomographic signals through the MUT 250 (including layers L1, L2, L3, etc. of the MUT 250). According to various embodiments, for any measurement, there is a two-electrode pairing including one transmitting and one receiving electrode (and, in this example up to three receiving electrodes). Based upon, for example, a known strength and frequency of the transmitted tomographic signal(s), a configuration of transmitting/receiving electrodes, a strength/frequency of the return tomographic signal(s), as well as a type of the MUT 250 (e.g., a general composition, known material properties, and/or a depth of penetration), various embodiments include determining characteristics (e.g., density, composition/sub-composition, etc.) of a portion (e.g., volume, sub-volume) of the MUT 250. Also illustrated are the measured volumes A12, A23, A34, B13, B 24, and C14 in the MUT 250. These measured volumes are related to the three layers of interest (L1, L2, L3) in the MUT 250. The equal center-to-center spacing of communicating electrodes (e.g., E1, E2, E3, E4) is determined by the thickness or depth of the layers (L1, L2, L3) of the MUT 250 that are to be characterized. FIG. 3 illustrates several close-up views of volumes A, B13 and C14 from FIG. 2. As shown, the depth into the MUT 250 that is detectable by the electrodes is approximately equal to one-half the spacing between the centers of communicating electrodes, D. FIG. 3 also provides an illustration of the size of the measured voxels A, B, and C. FIG. 4 is a schematic depiction illustrating the relative sizes of the measured voxels (C14, B13, A 12) along with the computed sub-voxels (a12, b 13 and c 14, respectively) from FIG. 2. The measured voxel A is the same size as the computed sub-voxel a; voxel B is twice the size of sub-voxel b; and voxel C is three times the size of sub-voxel c. FIG. 5 is a schematic depiction illustrating the arrangement of sub-voxels in a five-electrode array 500, which is used to describe more detail of the VDR approach according to various embodiments. It is understood that to characterize a greater number layers, a greater number of electrodes could be added to the array. For example in FIG. 5, a measured voxel D could be obtained by passing the signal between electrodes 1 and 5.

Figure 6:
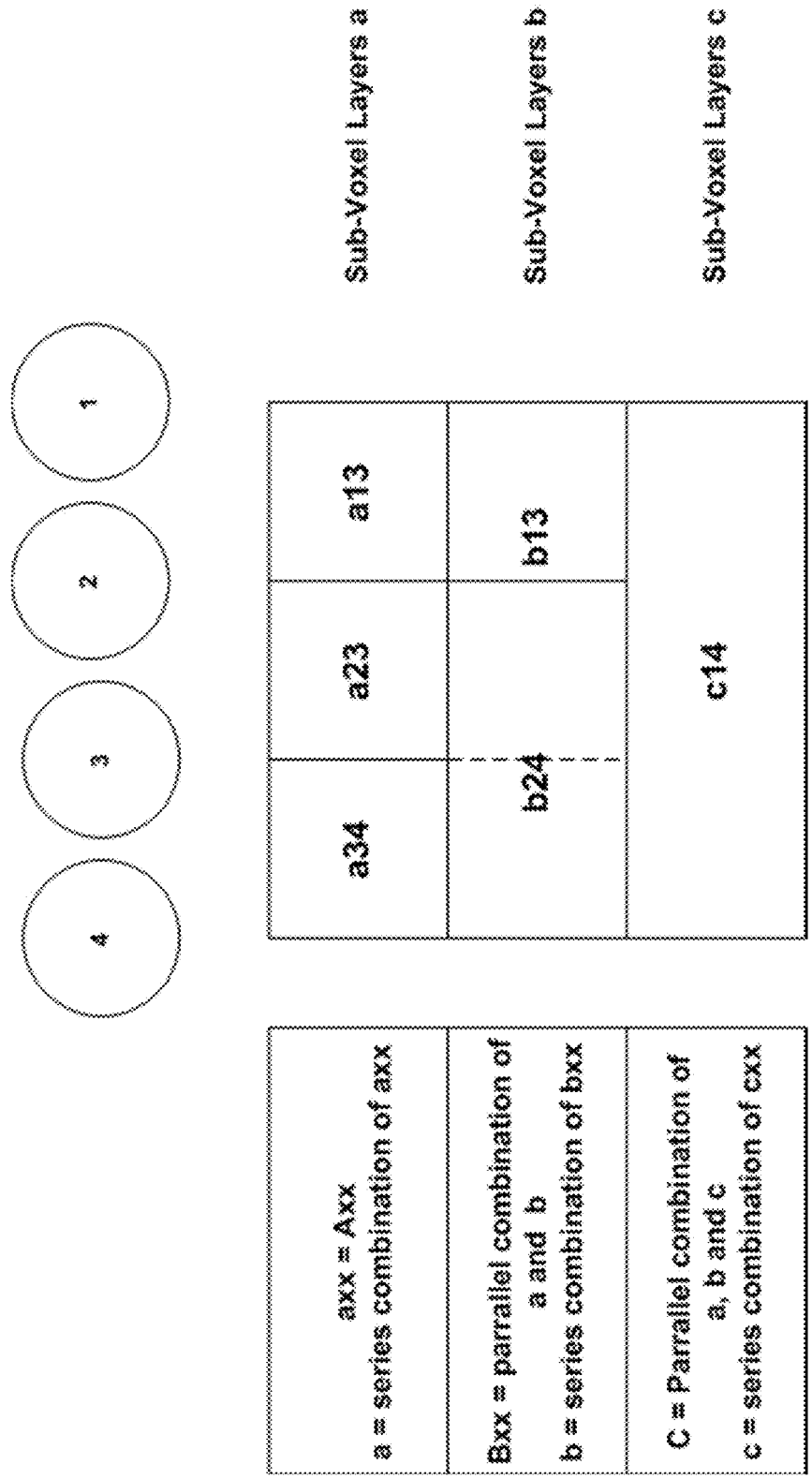
FIG. 6 is an illustration of the first level of measured and computed volumes with the relevant equations.
Figure 7:
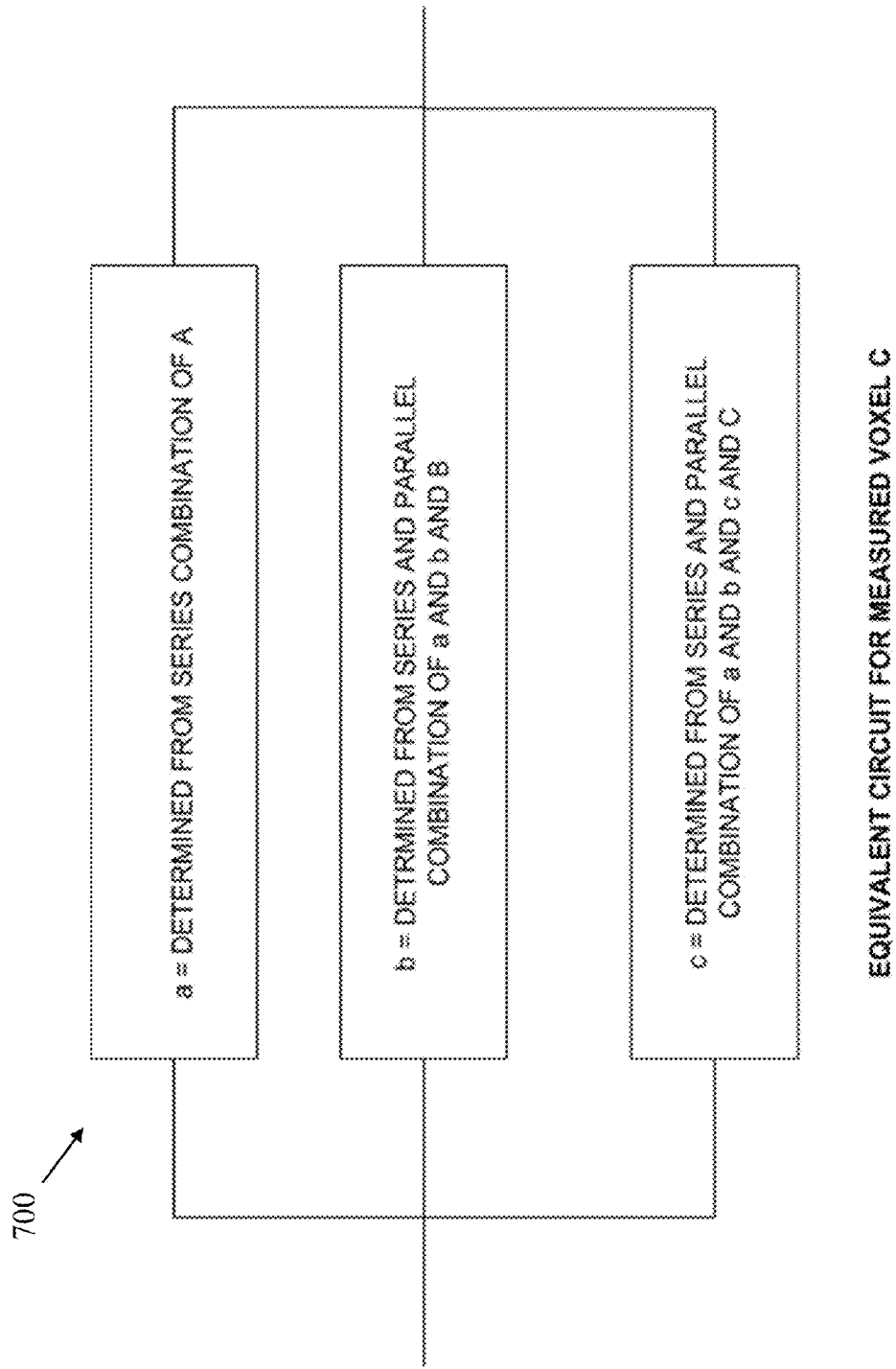
FIG. 7 is an illustration of the equivalent circuit used for the measured voxel C.

One approach according to various embodiments is to collect multiple two-electrode data and to compute the values of the sub-voxels from the voxel data, and to combine the sub-voxels into voxel segments to compute other sub-voxels using the voxel segments and the voxel data. This process is illustrated in the schematic diagram in FIG. 6, which illustrates sub-voxel layers a, b, and c, corresponding to a four-electrode array (where electrodes are indicated by circular elements 1, 2, 3 and 4, respectively) such as those shown and described with reference to FIGS. 5 and 6. The impedance values of sub-voxels axx are identical to voxel Axx. Assuming volumes B13 and B24 have equivalent physical properties and, therefore, impedance characteristics, the sub-voxels b13 and b24 are computed assuming b13 and b24 are in parallel with a13 and a 24. Sub-voxel a13 is the series combination of A12 and A23. Sub-voxel a24 is the series combination of A23 and A34. The sub-voxels are serially combined to form voxel segment b. Voxel segments a and b are combined in a parallel fashion with sub-voxel c14 to represent voxel C14. FIG. 7 illustrates a schematic depiction of the equivalent circuit model 700 for voxel C from FIG. 6. The equivalent circuit model 700 allows for the computation of sub-voxel c14 (FIG. 6). The mathematical process used to calculate the sub-voxel value c14 is illustrated in the equations and corresponding schematic depictions of the voxel/sub-voxel combinations shown in FIG. 8, FIG. 9, and FIG. 10.

Figure 8:
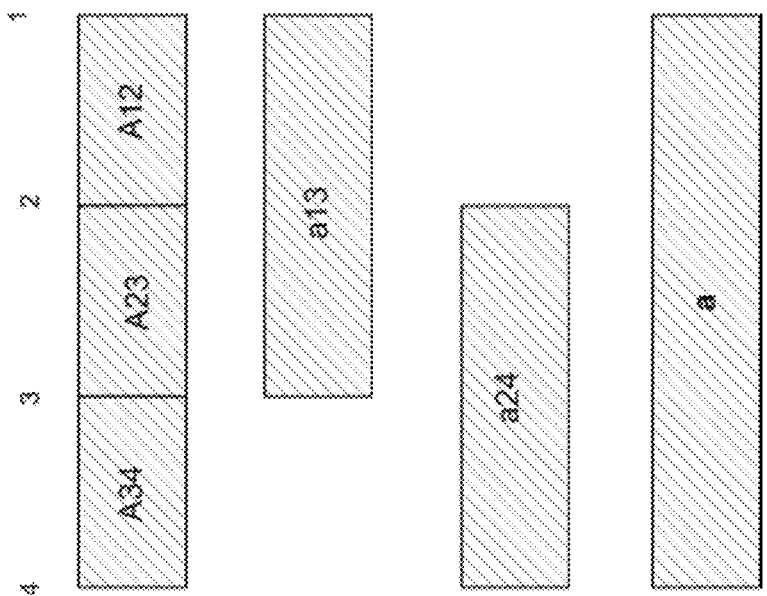
FIG. 8 is an illustration of the second level of measured and computed volumes with the relevant equations for Voxel A.
Figure 9:
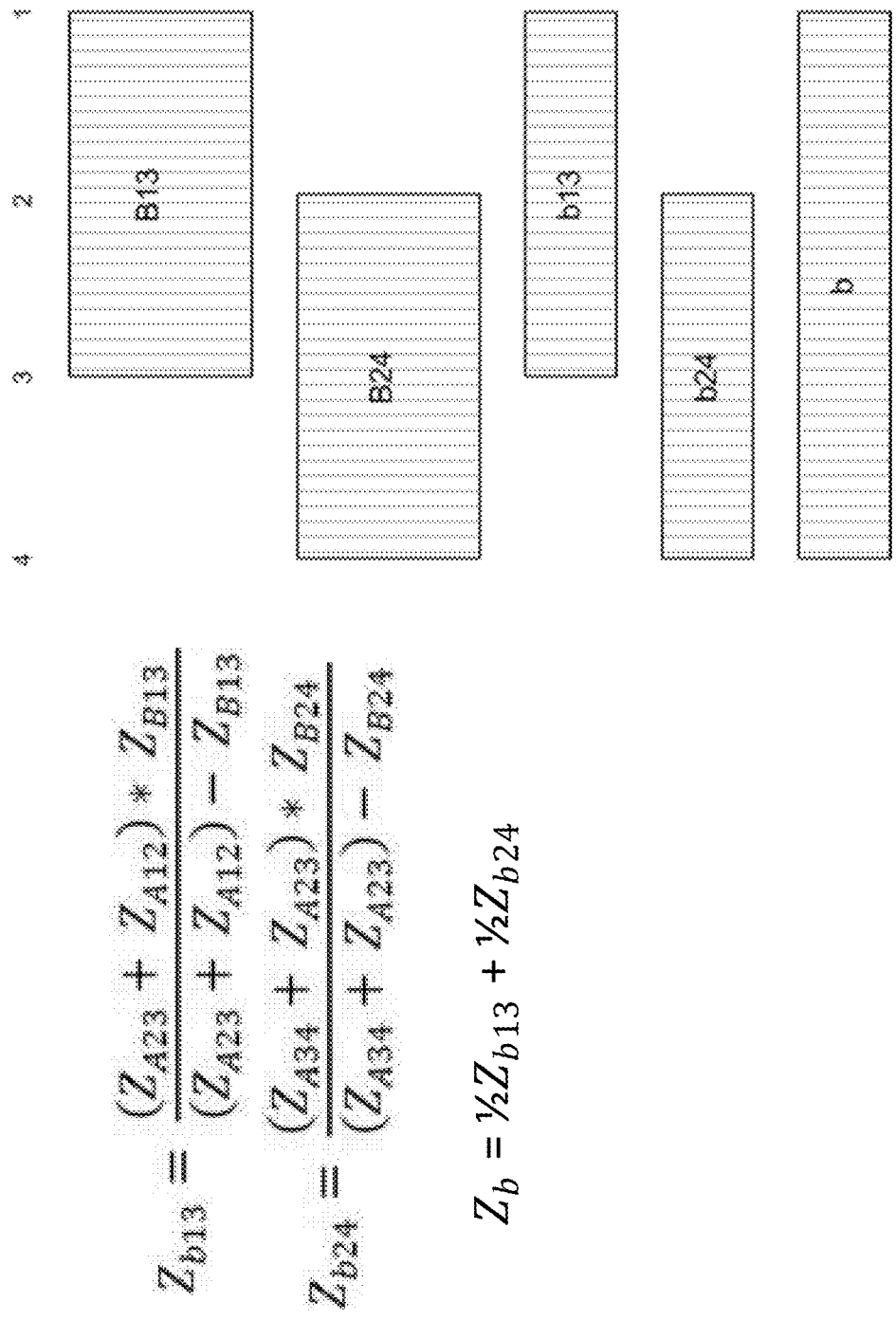
FIG. 9 is an illustration of the third level of measured and computed volumes with the relevant equations for Voxel B.
Figure 10:
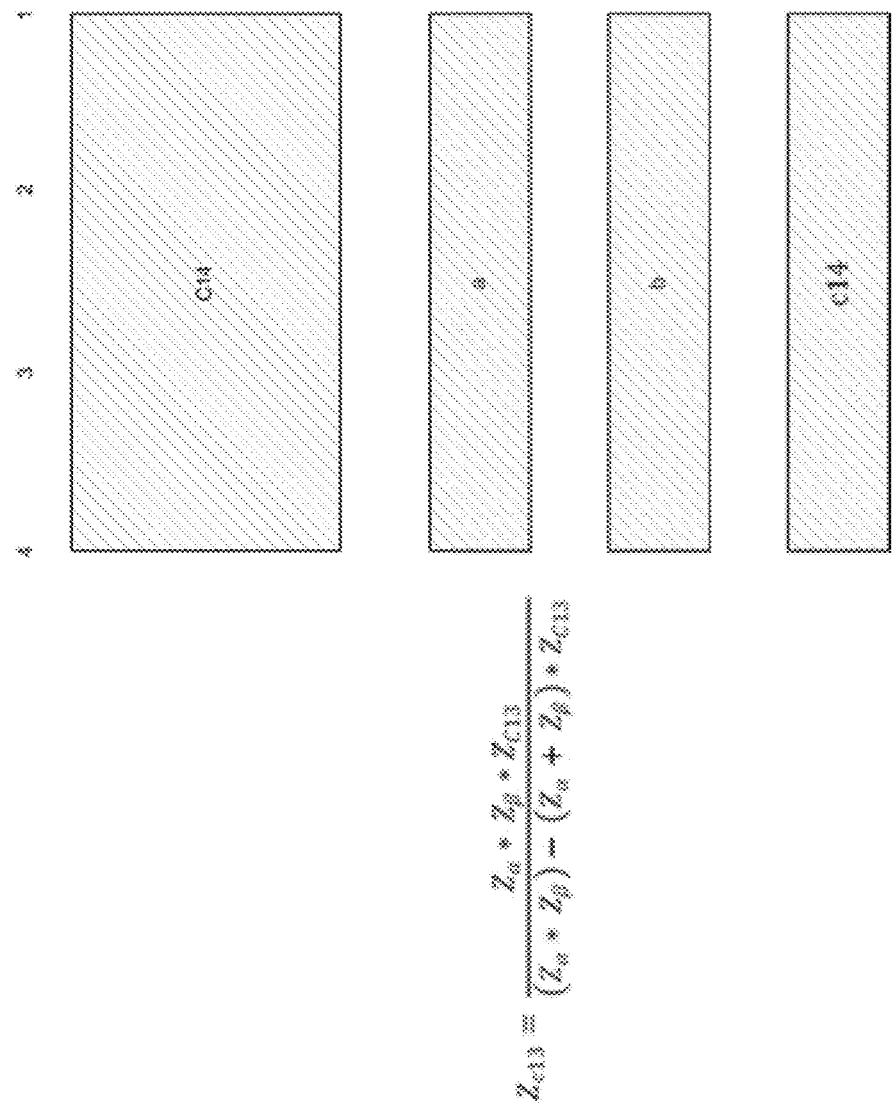
FIG. 10 is an illustration of the third level of measured and computed volumes with the relevant equations for Voxel C.

The general form of the equations depicted in FIGS. 8-10 according to various embodiments is presented as follows:

$$Z_{a(n,n+1)} = Z_{A(n,n+1)}$$

$$Z_{b(n,n+2)} = \frac{(Z_{A(n,n+1)} + Z_{A(n+1,n+2)}) * Z_{B(n,n+2)}}{(Z_{A(n,n+1)} + Z_{A(n+1,n+2)}) - Z_{B(n,n+2)}}$$

$$Z_{b(n+1,n+3)} = \frac{(Z_{A(n+1,n+2)} + Z_{A(n+2,n+3)}) * Z_{B(n+1,n+3)}}{(Z_{A(n+1,n+2)} + Z_{A(n+2,n+3)}) - Z_{B(n+1,n+3)}}$$

$$Z_{a(n,n+3)} = Z_{A(n,n+1)} + Z_{A(n+1,n+2)} + Z_{A(n+2,n+3)}$$

$$Z_{b(n,n+3)} = \alpha Z_{b(n,n+2)} + (1-\alpha) * Z_{b(n+1,n+3)}$$

$$Z_{c(n,n+3)} = \frac{Z_{a(n,n+3)} * Z_{b(n,n+3)} * Z_C(n, n+3)}{(Z_{a(n,n+3)} * Z_{b(n,n+3)}) - (Z_{a(n,n+3)} + Z_{b(n,n+3)}) * Z_{C(n,n+3)}}$$

According to various embodiments, the above equations may be modified based upon the geometry of the electrode arrangement to account for the differences between the measured volume of the MUT (e.g., MUT 250) and the assumed shape of the voxels and sub-voxels in that volume. To account for relative changes in the geometry of electrode arrangements, a geometry factor may be determined and applied to the measured impedance of the voxels as follows:

$$Z_{A(n,n+1)}$$

$$Z_{b(n,n+2)} = \frac{(\gamma_A Z_{A(n,n+1)} + \gamma_A Z_{A(n+1,n+2)}) * \gamma_B Z_{B(n,n+2)}}{(\gamma_A Z_{A(n,n+1)} + \gamma_A Z_{A(n+1,n+2)}) - \gamma_B Z_{B(n,n+2)}}$$

$$Z_{b(n+1,n+3)} = \frac{(\gamma_A Z_{A(n+1,n+2)} + \gamma_A Z_{A(n+2,n+3)}) * \gamma_B Z_{B(n+1,n+3)}}{(\gamma_A Z_{A(n+1,n+2)} + \gamma_A Z_{A(n+2,n+3)}) - \gamma_B Z_{B(n+1,n+3)}}$$

$$Z_{a(n,n+3)} = \gamma_A Z_{A(n,n+1)} + \gamma_A Z_{A(n+1,n+2)} + \gamma_A Z_{A(n+2,n+3)}$$

$$Z_{b(n,n+3)} = \alpha Z_{b(n,n+2)} + (1-\alpha) * Z_{b(n+1,n+3)}$$

$$Z_{c(n,n+3)} = \frac{Z_{a(n,n+3)} * Z_{b(n,n+3)} * \gamma_C Z_C(n, n+3)}{(Z_{a(n,n+3)} * Z_{b(n,n+3)}) - (Z_{a(n,n+3)} + Z_{b(n,n+3)}) * \gamma_C Z_{C(n,n+3)}}$$

where: A, B, and C are the measured voxel volumes;
a, b, and c are the computed sub-voxel properties;
n is the electrode array number;
α is the relative contribution of Z b(n+1, n+3) relative to Z b(n+1, n+3); and
$\gamma_x$ is a geometry factor for the xth voxel. The geometry factor is a correction applied to the planar electrodes to correlate the values read with a parallel plate electrode ∈. The parallel plate equation is:

$$C = \frac{A}{d}\varepsilon;$$

where:
C is the capacitance;
∈ is the dielectric; and
A/d is equivalent to the geometry factor.

The ability to secure the impedance measurements used to apply the above disclosed VDR methodology as explained above can depend upon the corresponding design and operation of the sensor array. Some array designs have been previously disclosed in the above-referenced issued patents and patent applications. In the following paragraphs, five linear and planar electrode array configurations are presented which provide various improvements over the those referenced patents and patent applications. As indicated above, the VDR is applied to compute the impedance for each sub-voxel at each frequency in the range of applied frequencies to secure the impedance characteristics of each sub-voxel at each frequency. These data may then applied using various spectrographic methods to characterize the desired property or properties of the MUT.

Figure 11:
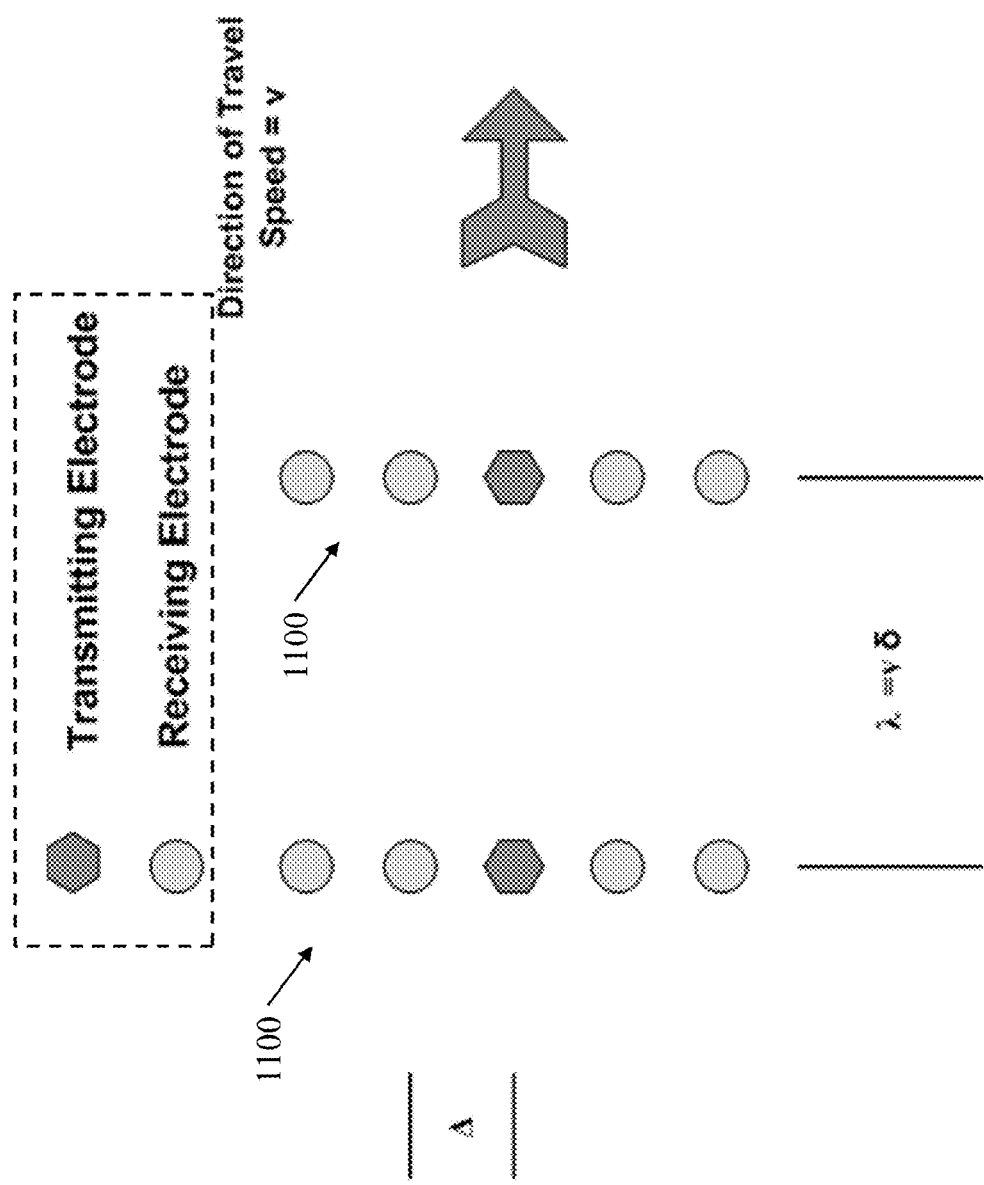
FIG. 11 is an illustration of a moving linear array
Figure 12:
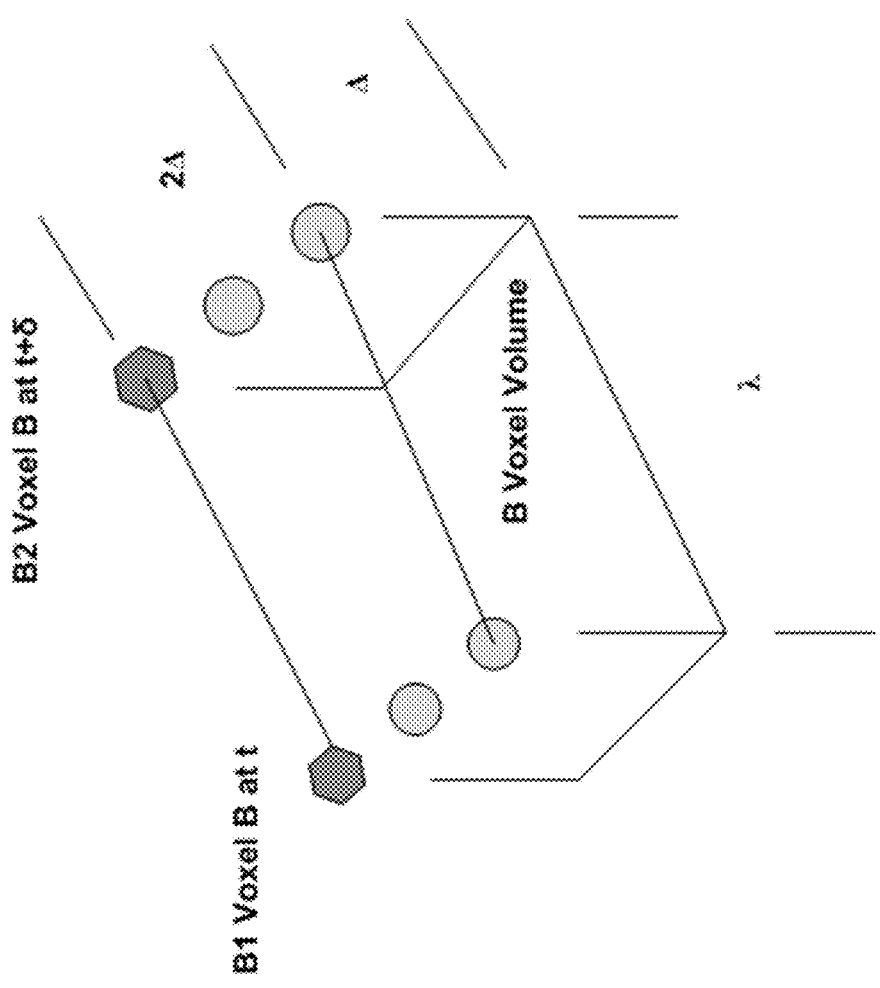
FIG. 12 is an illustration of a three dimensional voxel derived from the movement of a linear array.

In U.S. provisional patent application No. 61/703,488, the movement of a sensor array is discussed as a method to detect features in an MUT. FIG. 11 illustrates the movement of a five electrode array 1100 with a fixed arrangement of transmitting and receiving electrodes. The array 1100 has an electrode center-to-center spacing of Δ, and is traveling at a speed of v. Data is secured in time intervals of δ. Over the time interval, the array moves a distance of λ=vδ. For a B voxel, two measurements at time t and t+δ yields a three-dimensional voxel as shown in the schematic depiction of voxel B in FIG. 12. As illustrated in FIG. 12, voxel B is 2Δ wide, Δ deep and λ long. In this embodiment, the impedance characteristics of this three dimensional voxel, $\overline{B}$, is given by a series combination of the $B_t$ and the $B_{t+\delta}$ voxels, with a geometric correction factor which will vary with the size of the electrodes and the size of λ. This geometric scaling may be experimentally determined, and represented as:

$$\overline{B} = B_t + B_{t+\delta};$$

Once the impedance characteristic of the three dimensional voxels are determined, the sub-voxel information may be determined in the same manner as described above.

Figure 13:
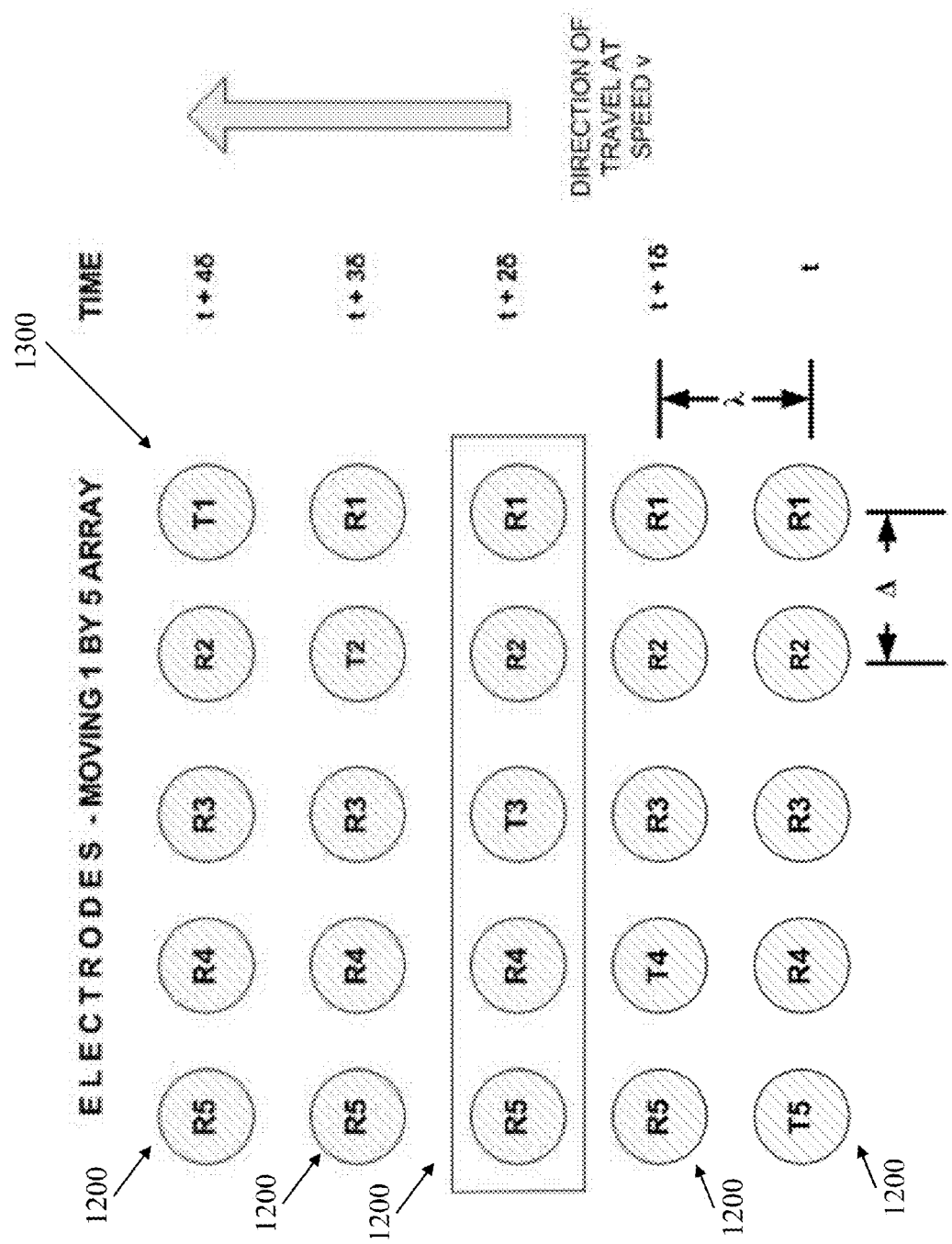
FIG. 13 is an illustration of a moving linear array with the transmitting electrode change every time period 6.
Figure 14:
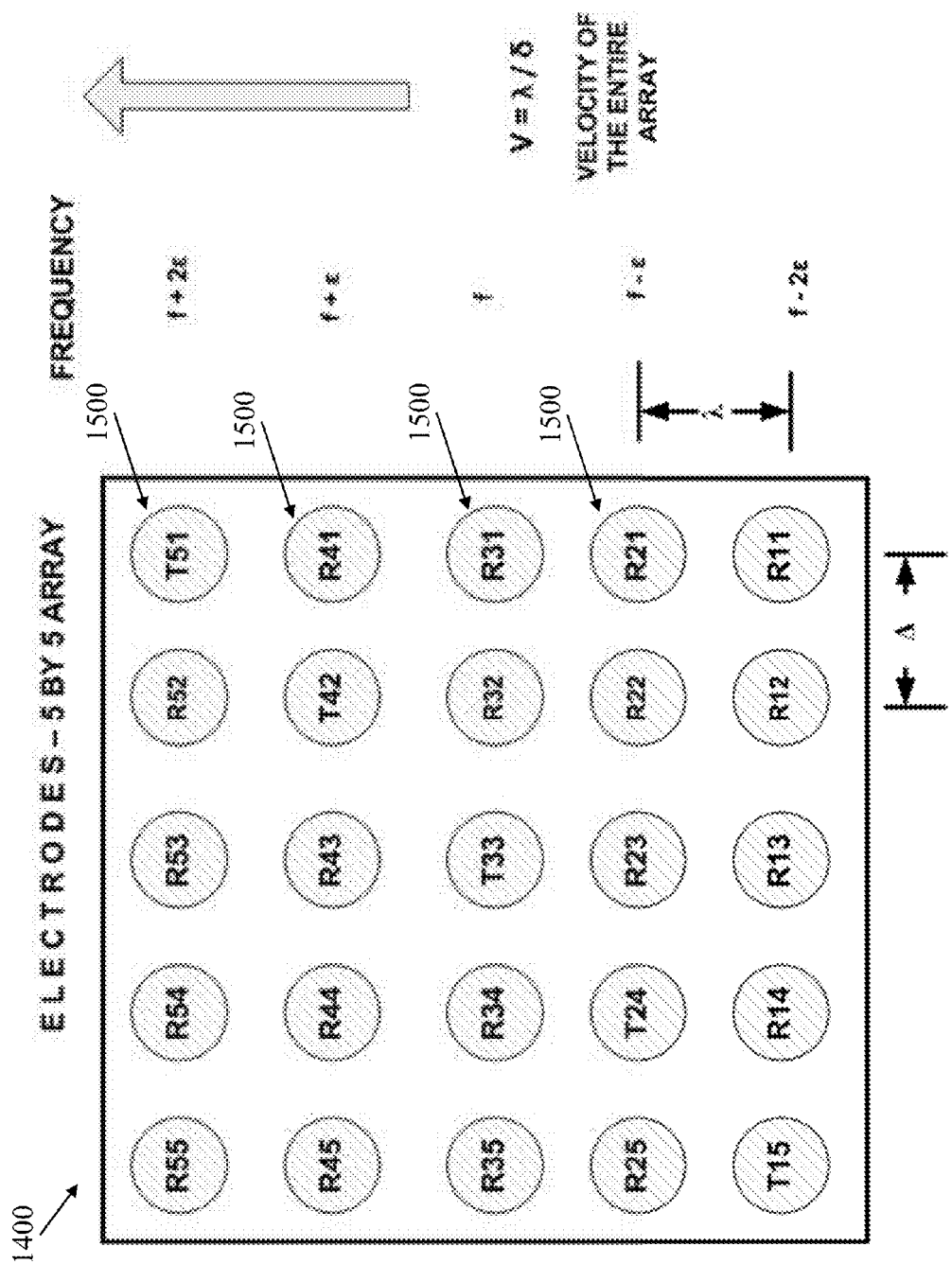
FIG. 14 is an illustration of a square planar electrode array where each linear electrode array is operating at a different frequency.

The approach described with reference to FIGS. 11-12 may fail if the transmitting and receiving electrode spacing are varied (not constant). As previously discussed in conjunction with FIG. 2, according to various embodiments, each electrode in an array may either transmit or receive. This bi-modal concept is illustrated in the schematic depiction of several five-by-one linear arrays 1200 in a larger planar array 1300 (including each of the five-by-one arrays 1200) in FIG. 13. As shown, a five-electrode linear arrays 1200 scan through the five options for the transmitting electrode (T1, T2, T3, T4, T5) while the planar array 1300 is moving at a velocity of v. According to various embodiments, the transmitting electrode (TX) is switched every 6 second, such that each of the five electrodes in each linear array 1200 is transmitting over the five time intervals of measurement. In this example, according to various embodiments, the distance traveled during the transmitting electrode switching process is λ=5vδ. Applicants have discovered that the size of λ may affect the ability to apply the method described above to accurately characterize the MUT (e.g., MUT 250) if changes in physical properties (e.g., density, composition, viscosity, etc.) occur in the MUT at the same scale or smaller than λ. This change in the MUT, according to various embodiments, can be used to determine the characteristic(s) of the MUT, and the detail at which the MUT may be examined. The time duration δ is dependent on the speed at which the planar array 1300 (including linear arrays 1200) is moving, the speed at which the array electronics can switch between transmitting electrodes, and the time required to process the measurement data to characterize the MUT (e.g., where processing is performed using at least one computing device, as described herein with reference to FIG. 19). The number of electrodes in the array can also affect the determination of λ. An alternate embodiment of an array 1400 is schematically depicted in FIG. 14. In this embodiment, the array 1400 includes a planar array composed of five rows of linear five-electrode arrays 1500, depicted as moving at a velocity, v. The transmitting electrode (TXX) in each linear array 1500 is fixed, while each transmitting linear array 1500 is operated at a different frequency with a separation of c Hz. This frequency separation is sized such that the signals from distinct linear arrays 1500 may be isolated electronically, and such that the total change in frequency does not result in a change in the interpretation of the physical parameters of the MUT that are of interest. In various embodiments, the number of rows of linear arrays 1500 in the planar array 1400 is equal to the number of electrodes in each of the linear arrays 1500 (e.g., 5 rows of linear arrays 1500 with 5 electrodes each).

Figure 15:
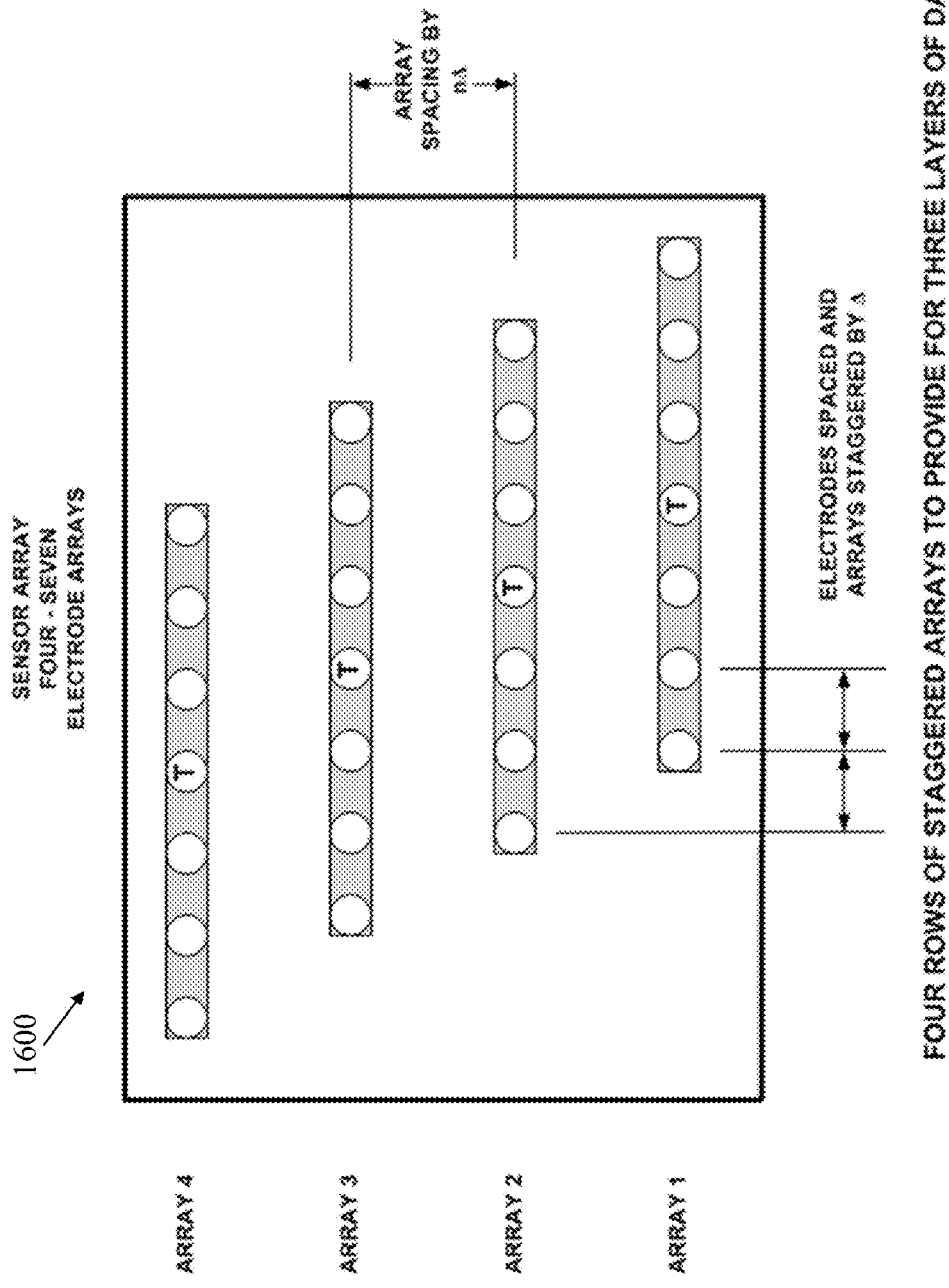
FIG. 15 is an illustration of a planar array consisting of staggered linear electrodes.
Figure 16:
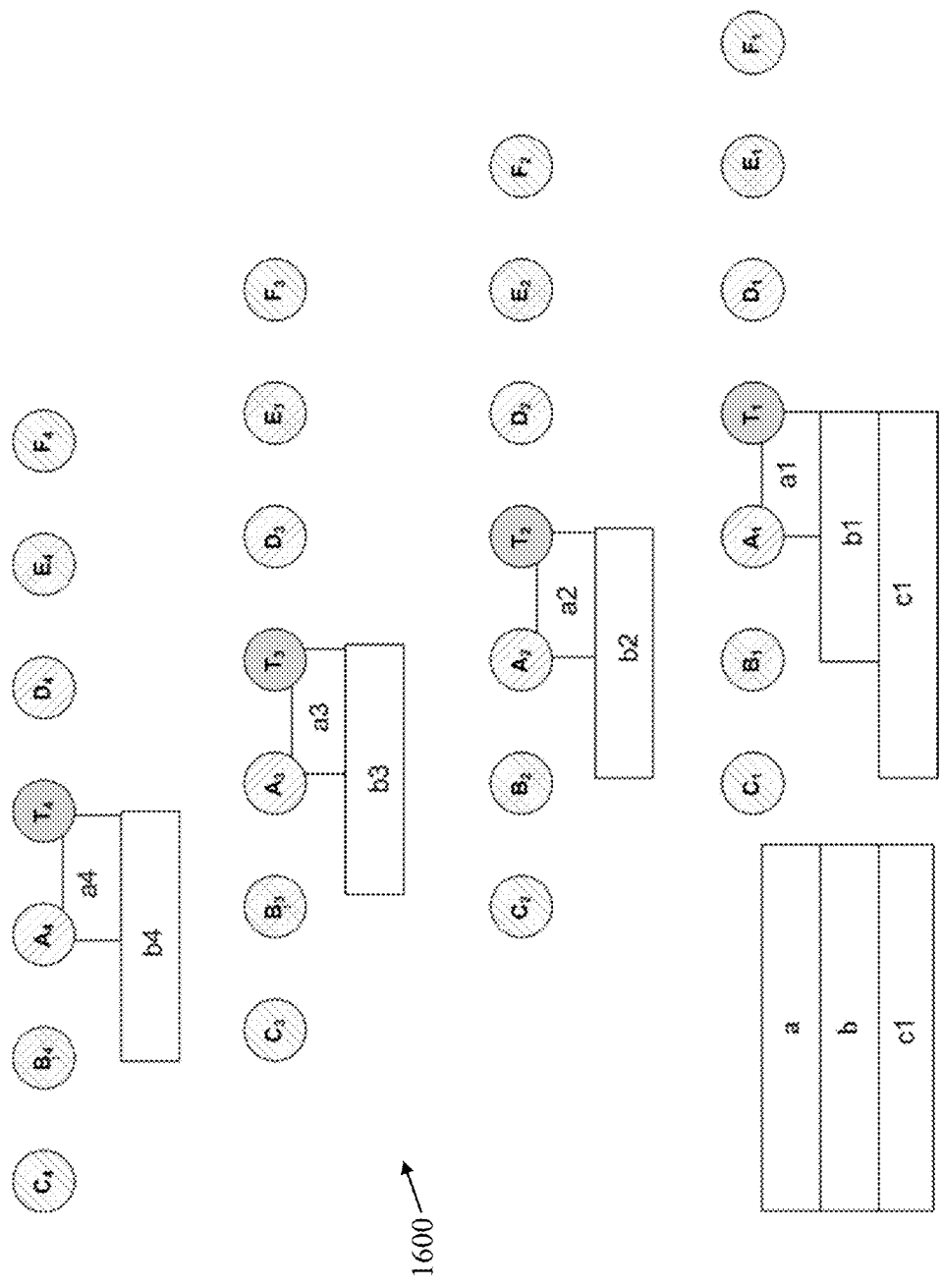
FIG. 16 is an illustration of the method of generating the required voxel data for determination of sub-voxel characteristics.

An alternative embodiment of a planar array 1600 is shown in FIG. 15, which uses four linear arrays (Array 1, Array 2, Array 3, Array 4) orientated with each array (1, 2, 3, 4) being offset from its adjacent array (1, 2, 3, 4) by the center-to-center spacing between adjacent electrodes in each of Array 1, Array 2, Array 3 and Array 4. If variations in the properties of the MUT are small in the horizontal plane relative to the size of the planar array 1600, this alternative embodiment may be beneficial in determining characteristics of the MUT. Further, if the thickness of the MUT (e.g., thickness of particular layers or overall thickness) is small, this embodiment can enable accurate measurement of the MUT. For example, some coatings are placed on critical parts in machinery, with each coating thickness on the order of 50 microns. In this example, the electrode spacing (in each Array) can be on the order of approximately 50 microns in order to see at least two layers of the coating. The total size of the planar sensor array 1600 with four seven-electrode linear arrays (Array 1, Array 2, Array 3, Array 4) can be on the order of approximately 500 microns (0.02 inches) squared. In this type of planar array 1600, the number of electrodes in each array (Array 1, Array 2, etc.) is an odd number, and the transmitting electrode (T) is fixed as the middle electrode in each array (Array 3, Array 4, etc.). FIG. 16 is a schematic depiction of the planar array 1600 of FIG. 15, further illustrating how characteristics of the sub-voxels (e.g., b4, b3, b2, etc.) can be determined from this type of array 1600 according to various embodiments described herein. In this type of array 1600, according to some embodiments, each of the seven-electrode linear arrays (Array 1, Array 2, etc.) may be operated at different times, with the same frequency. In some embodiments, the seven-electrode linear arrays (Array 1, Array 2, etc.) may be operated simultaneously at slightly different frequencies, as described with reference to various embodiments described herein.

Figure 17:
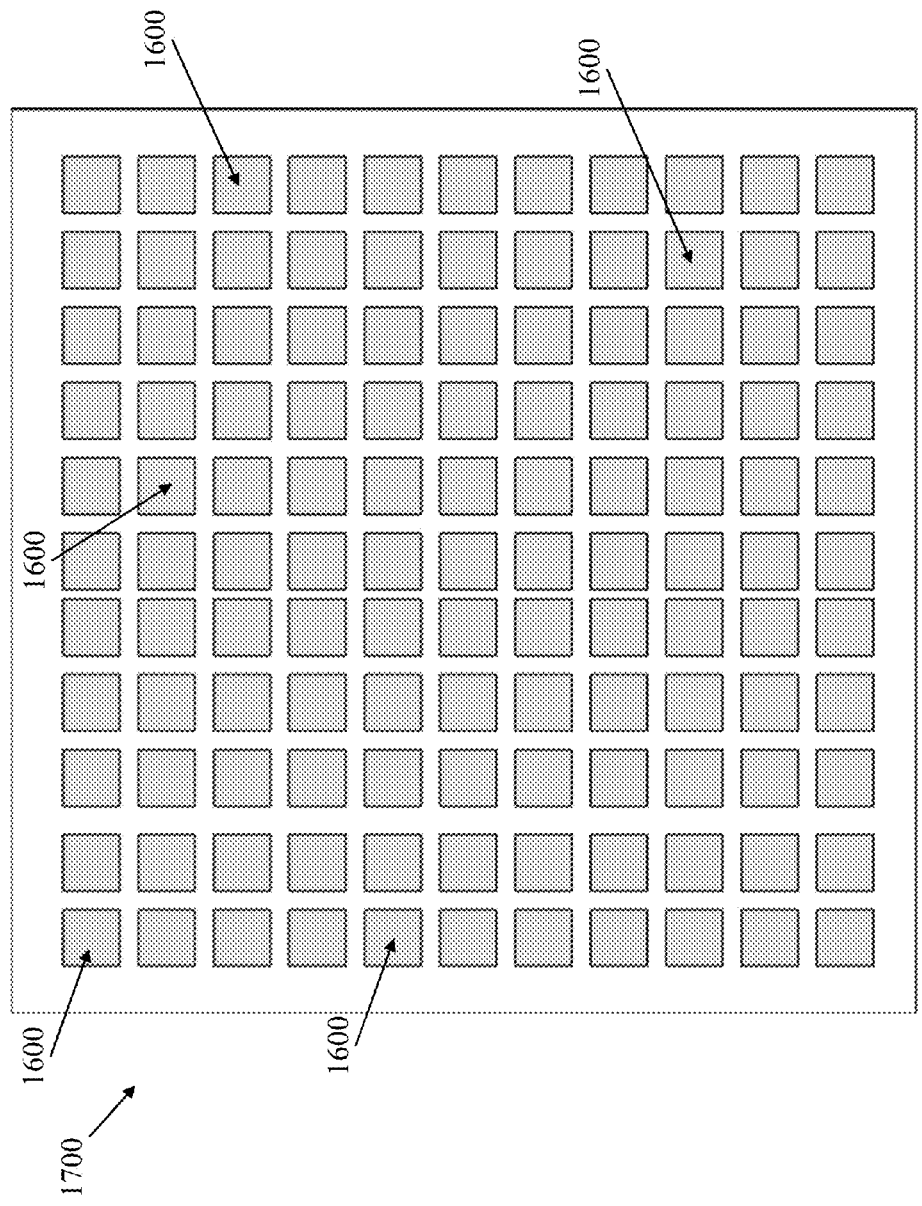
FIG. 17 is an illustration of the placement of individual planar sensor arrays onto a large inspection matrix.

Given the potentially very small size of the planar array 1600 in order to detect relatively thin regions of an MUT, a method to cover larger areas of the MUT can include combining a number of the relatively smaller planar arrays 1600 located on a lager inspection fixture 1700, depicted schematically in FIG. 17. In this example illustration, the inspection fixture 1700 includes 121 of the planar arrays 1600 of FIGS. 15-16, located on a one-inch grid. According to various embodiments, many methods are available to scan through the planar arrays 1600 to determine characteristics of the MUT. For example, each planar array 1600 may be treated as a pixel, and can be scanned by any of the various available electronic scanning methods known in the art.

Figure 18:
FIG. 18 shows schematic depictions of example electrode shapes according to various embodiments.
Figure 18:
Figure 18:
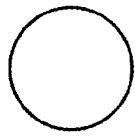

The design of the individual electrodes in the various arrays discussed with reference to FIGS. 1-17 may be circular in shape. However, in some embodiments, a circular-shaped electrode may limit the potential of field concentration available if the desired area of detection in the MUT included a corner or a point. In various embodiments, at least one of the electrodes has an ellipsoid shape. In various other embodiments, at least one of the electrodes has a rectangular shape with rounded corners. FIG. 18 shows schematic depictions of example electrode shapes, which can be used in any of the electrode arrays shown and described herein according to various embodiments. The Applicants have also found that field concentrations may distort the electromagnetic field and affect the raw data obtained from the MUT. Accordingly, in various embodiments, the electrodes may have a uniform area to match their signal generation capacity with corresponding receiving capacity. In some cases, the diameter of the electrodes relative to the distance between the center of the electrodes, $\Delta$, may vary. The Applicants have further discovered that there may be a tradeoff between the electromagnetic field strength of the array, the geometry factor of the array, and the signal-to-noise ratio of the measurement obtained by the array. Applicants have further discovered that these factors are not determinant a priori to establish the optimum area of the electrode.

Various approaches described allow for determining a physical property of a sub-voxel or a number of sub-voxels of the MUT. In various embodiments, a number of measurements of the physical property(ies) of interest are measured by conventional means and correlated with the measured variations of the measured (and computed) complex impedance (of the voxels and sub-voxels) using the arrays/systems/approaches described herein. In various embodiments, the number of measurements can be sufficiently large such that the resulting correlation is statistically significant. The impedance measurements can be made with the same type of array that will be used to inspect unknown MUTs, or in other embodiments, a parallel plate electrode arrangement may be used. Regardless of the array geometry, the measurements may also be made over a range of frequencies. Further embodiments include a method of developing an algorithm to correlate the physical property to the measured impedance (of the voxel or sub-voxel over the selected range of frequencies), which may use any number of well known correlation methods such as analysis of variations (ANOVA), neural networks, and multiple regressions. A determination as to which process, impedance characteristic(s) and frequency range may ensure that the best fit may be made by selection of the one that provides the most statistically significant results.

Figure 19:
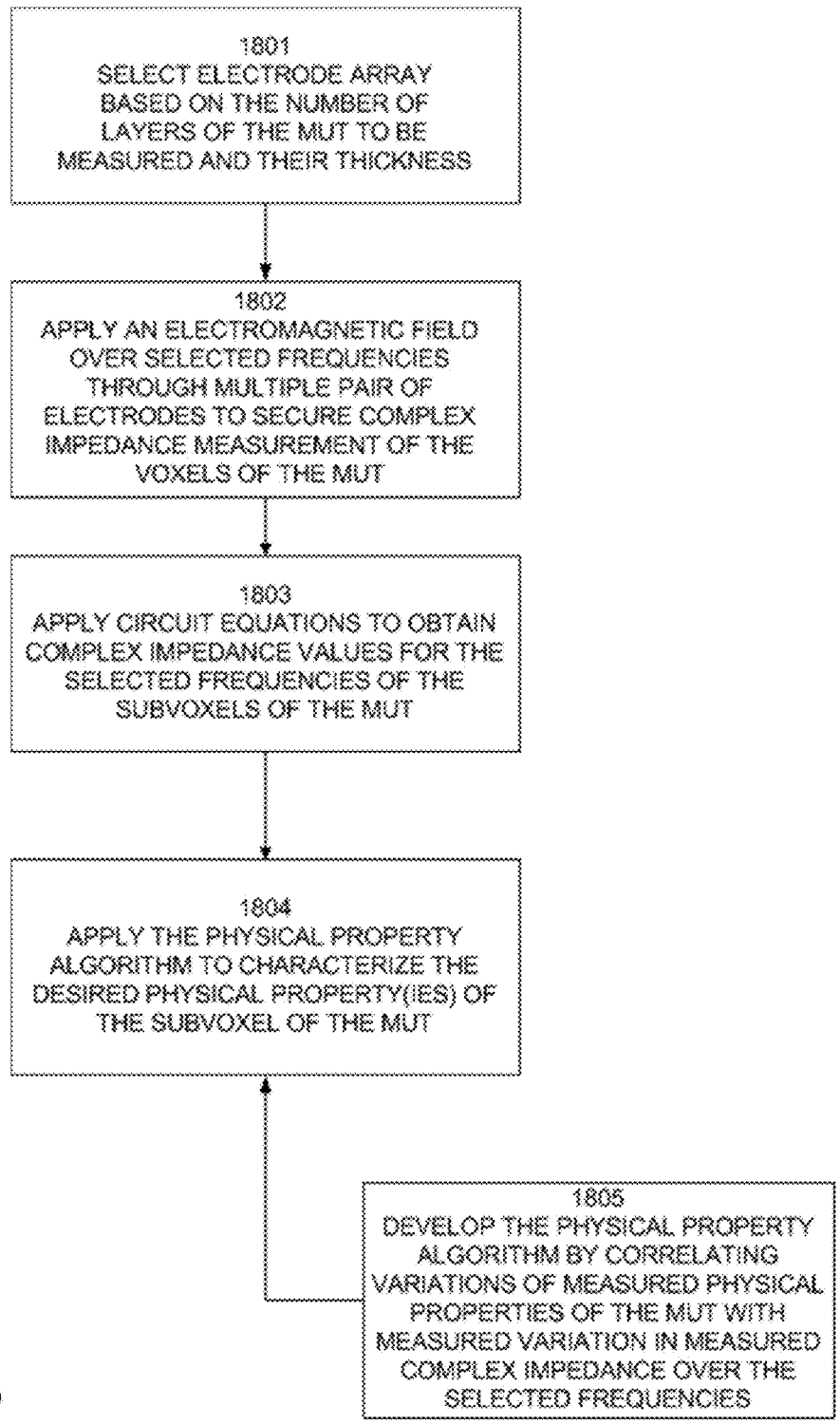
FIG. 19 is a flow chart illustrating a process according to various embodiments.
Figure 20:
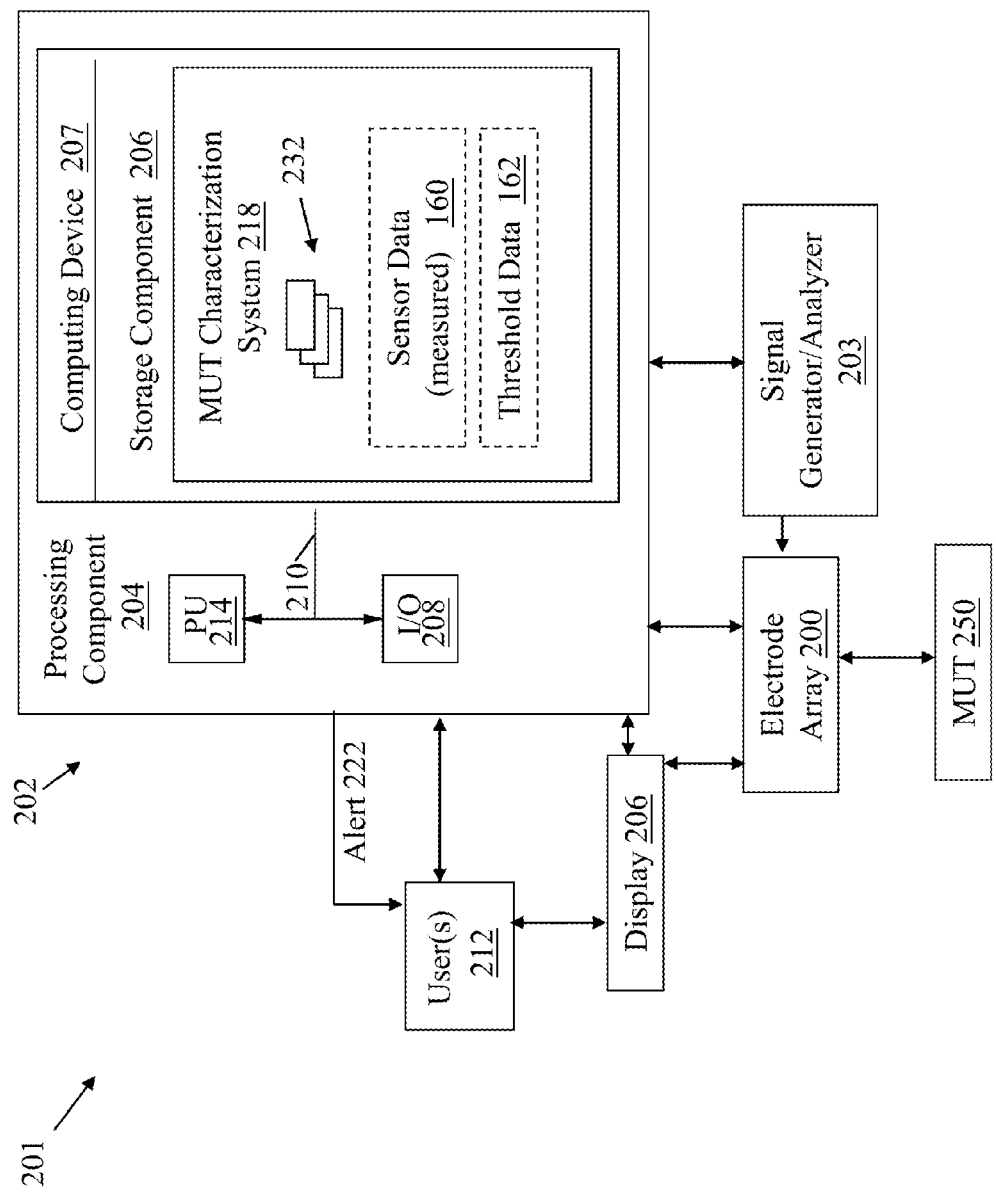
FIG. 20 shows a schematic depiction of an environment including a system according to various embodiments.

FIG. 19 presents a flow diagram illustrating processes to determine at least one characteristic (e.g., physical property) of a sub-voxel of a MUT (e.g., MUT 250, FIG. 1, FIG. 20). The first process (1801) can include selecting the appropriate type of array for use with the MUT, and selecting the number and thickness of each layer that is to be measured, along with an overall thickness of the layers to be measured. The number and thickness of individual layers, as well as overall thickness, can determine the number of electrodes in the array, and the corresponding center-to-center spacing of adjacent electrodes useful to detect characteristics of the MUT. The next process (1802) can include coupling the sensor array to an impedance measuring system (e.g., at least one computing device) to obtain the complex impedance values for the voxels of interest in the MUT. The measurements can be made over the frequency range that corresponds with the required inputs to the physical property algorithm. The next process (1803) includes utilizing the circuit equations described according to various embodiments herein to compute the desired impedance characteristic of the sub-voxels, over the frequency range that corresponds with the required inputs to the physical property algorithm. The final process in this method (1804) can include using the sub-voxel impedance values (along with the physical property algorithm described according to various embodiments) to determine the corresponding characteristic (e.g., physical property) of that sub-voxel of the MUT. An optional additional process (1805) can include developing the physical property algorithm which is applied in step 1804, prior to applying that algorithm.

Figure 21:
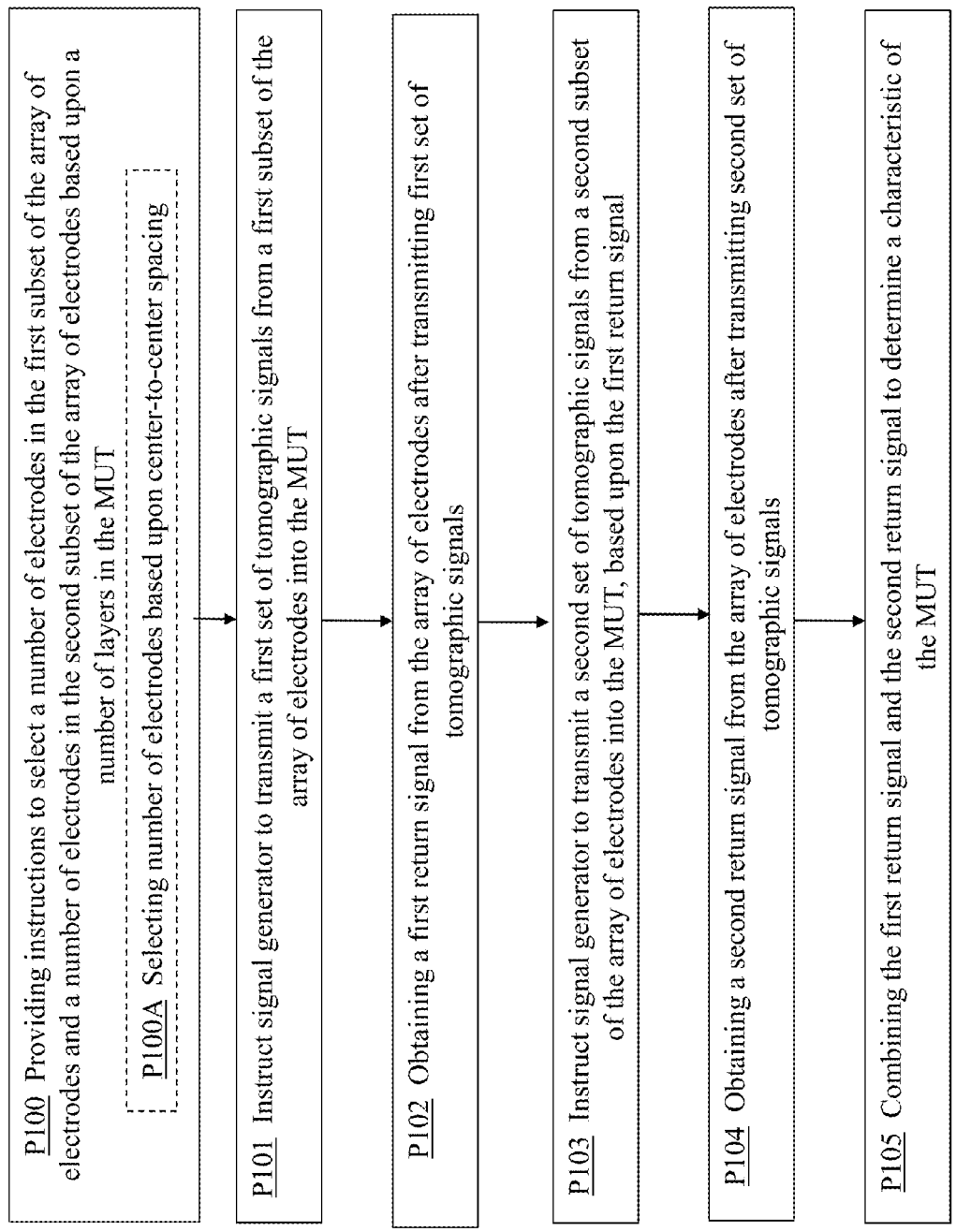
FIG. 21 shows a flow chart illustrating a process according to various embodiments.

As described herein, various aspects of the invention can include computer implemented methods, systems and computer program products for performing a series of functions. In some cases, as shown in FIG. 20, a system 201 is described which includes an array of electrodes 200 for communicating (conductively or non-conductively) with a surface and a subsurface beneath the surface of a MUT 250. As described herein, the array of electrodes 200 can be configured in a plurality of distinct ways to detect, and potentially determine the characteristics of, an MUT 250. The system 201 can further include a signal generator (e.g., operating over a range of frequencies and in some cases including an analyzer) 203 operably connected (e.g., hardwired) with the array of electrodes 200. The system 201 can further include at least one computing device 207 operably connected with the signal generator 203 (e.g., wirelessly and/or hard-wired) and the array of electrodes 200 (e.g., wirelessly and/or hard-wired, or simply via common connection with the signal generator). Referring to FIG. 20, the at least one computing device 207 is configured to perform the following processes (not necessarily in this order):

FIG. 21 shows a flow diagram depicting a method according to various embodiments of the disclosure. The method can be used to characterize select volumes of an MUT using an array of electrodes. As shown, the flow diagram can include processes including:

Process P101: instructing a signal generator 203 to transmit a first set of tomographic signals from a subset of the array of electrodes 200 into the MUT 250 and obtain the return signal at that frequency for that subset of the array of electrodes;

Process P102: obtaining a first return signal from the array of electrodes 200 after the transmitting of the first set of tomographic signals;

Process P103: instructing the signal generator 203 to transmit a second set of tomographic signals from a second subset of the array of electrodes 200 into the MUT 250 based upon the first return signal, the second subset of the array of electrodes including at least one electrode not included in the first subset of the array of electrodes. Referring to FIGS. 15-16, an example scenario illustrating distinct subsets in the array of electrodes 200 can include a first subset of electrodes, e.g., array 4, and a second subset of electrodes, e.g., array 2, array 3 or array 1. In some cases, these individual arrays (array 1, array 2, etc.) are deemed "sub-arrays" in an overall planar array (as shown in FIG. 15); According to some embodiments, sub-arrays can include overlapping electrodes, with at least one electrode present in a first sub-array that is not present in a second sub-array;

Process P104: obtaining a second return signal from the array of electrodes 200 after the transmitting of the second set of tomographic signals; and Process P105: combining the first return signal and the second return signal to determine a characteristic of the MUT 250. According to various embodiments, the first return signal and the second return signal each include complex impedance data about at least one of a volume or a voxel of the MUT 250. In some embodiments, the combining of the first return signal and the second return signal to determine a characteristic of the MUT 250 includes applying at least one of series or parallel circuit theory to the complex impedance data based upon a location of the first subset of the array of electrodes and the second subset of the array of electrodes in the electrode array 200. The series and parallel circuit approach is described with respect to various embodiments herein. According to various embodiments, the complex impedance data about the at least one of the volume or the voxel is correlated with physical properties of the MUT 250.

In various embodiments, prior to process P101, preliminary process P100 can include providing instructions to select a number of electrodes in the first subset of the array of electrodes 200 and a number of electrodes in the second subset of the array of electrodes 200 based upon a number of layers in the MUT 250. In various embodiments, this preliminary process P100 can include Process P100A: selecting the number of electrodes in the first subset and the number of electrodes in the second subset based upon a center-to-center spacing between adjacent electrodes in the array of electrodes.

As noted herein, according to various embodiments the array of electrodes (electrode array 200) includes a linear array of equally spaced electrodes configured to operate at a single frequency. Further, in some embodiments, the instructing of the signal generator 203 to transmit the first set of tomographic signals, the obtaining of the first return signal, the instruction of the signal generator 203 to transmit the second set of tomographic signals, and the obtaining of the second return signal are performed while the electrode array 200 is in motion parallel to a plane co-planar with the array of electrodes 200, and wherein the first return signal and the second return signal are separated at a time interval, δ.

Figure 22:
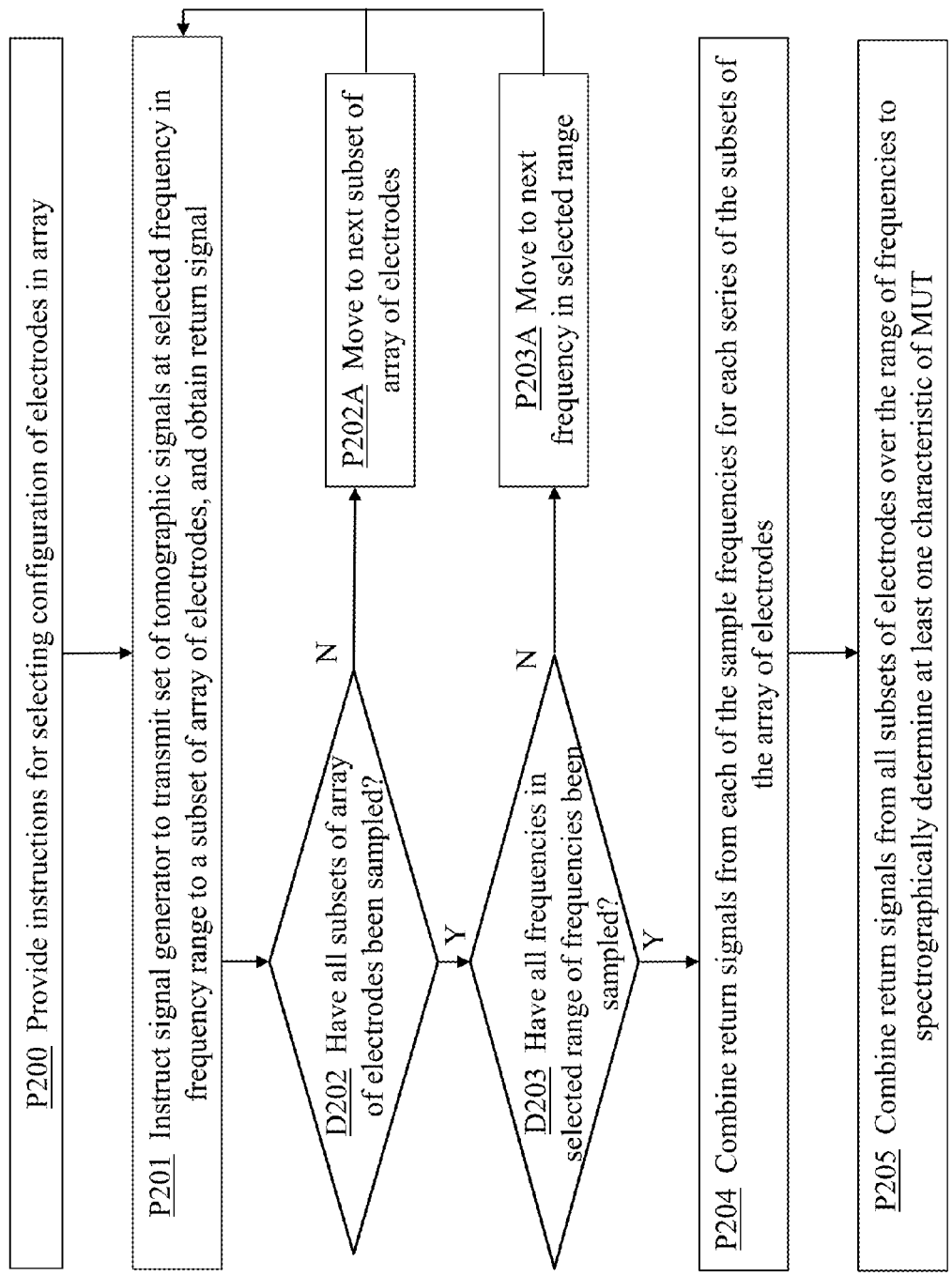
FIG. 22 shows a flow chart illustrating a process according to various embodiments.

FIG. 22 shows an illustrative flow diagram depicting a method according to various embodiments. The method can include:

Process P200: Providing instructions for selecting a configuration of electrodes 200 in the array of electrodes 200, including electrode subsets, based upon at least one of: A) Number of layers in the MUT 250; B) Center-to-center spacing between electrodes 200 based upon the thickness of the MUT 250; C) Frequency range of data collection based upon the spectrographic impedance characteristics of desired MUT 250 property/properties; and/or D) Subset arrangements of the array of electrodes 200, based upon requirements of the application of the series and/or parallel circuit approach to compute the complex impedance for each voxel and/or subvoxel of the MUT 250;

P201: Instructing signal generator 203 to transmit set of tomographic signals at selected frequency in frequency range to a subset of the array of electrodes 203, obtain return signal;

D202: Have all subsets of array of electrodes 200 been sampled?;

P202A: No to D201A, move to next subset of array of electrodes 200; loop back to P201;

D203: Yes to D201A, have all frequencies in the selected range of frequencies been sampled?;

P203A: No to D203, move to the next frequency in the selected range of frequencies, loop back to P201;

P204: Combine return signals from each of the sample frequencies for each series of the subsets of the array of electrodes 200, using series and/or parallel equivalent circuit approach described herein to compute complex impedance for each voxel and/or sub-voxel of MUT 250; and P205: Combine return signals from all subsets of electrodes 200 over the range of frequencies to spectrographically determine at least one physical characteristic of the MUT 250.

Returning to FIG. 20, the system 201 for characterizing select volumes of a material under test (MUT) by performing processes described herein with respect to various embodiments is shown in greater detail. To this extent, the system 201 includes a computer system 202 that can perform one or more processes described herein in order to control operation of a sensor array system (e.g., electrode array 200, such as those shown and described with reference to FIGS. 13-17), a signal generator/analyzer 203, and/or a display 206. In particular, the computer system 202 is shown as including an MUT characterization system 218, which makes computer system 202 operable to characterize an MUT (including a surface/subsurface) by performing any/all of the processes described herein and implementing any/all of the embodiments described herein.

The computer system 202 is shown including the computing device 207, which can include a processing component 204 (e.g., one or more processors), a storage component 206 (e.g., a storage hierarchy), an input/output (I/O) component 208 (e.g., one or more I/O interfaces and/or devices), and a communications pathway 210. In general, the processing component 204 executes program code, such as the MUT characterization system 218, which is at least partially fixed in the storage component 206. While executing program code, the processing component 204 can process data, which can result in reading and/or writing transformed data from/to the storage component 206 and/or the I/O component 208 for further processing. The pathway 210 provides a communications link between each of the components in the computer system 202. The I/O component 208 can comprise one or more human I/O devices, which enable a user (e.g., a human and/or computerized user) 212 to interact with the computer system 202 and/or one or more communications devices to enable the system user 212 to communicate with the computer system 202 using any type of communications link. To this extent, the MUT characterization system 218 can manage a set of interfaces (e.g., graphical user interface(s), application program interface, etc.) that enable human and/or system users 212 to interact with the MUT characterization system 218. Further, the MUT characterization system 218 can manage (e.g., store, retrieve, create, manipulate, organize, present, etc.) data, such as sensor data 160 and/or threshold data 162 using any solution. It is understood that the sensor data 160 can include data obtained by the sensor array 200 about the MUT 250. Threshold data 162 can include data representing one or more thresholds used to determine a characteristic of the MUT 250. That is, the threshold data 162 can be based upon predetermined conditions which account for a threshold level of tomographic and/or spectrographic differential between the output signals and the return signals. The MUT characterization system 218 can additionally communicate with the electrode array 200, signal generator/analyzer 203, the user 112 and/or display 106, e.g., via wireless and/or hardwired means.

In any event, the computer system 202 can comprise one or more general purpose computing articles of manufacture (e.g., computing devices) capable of executing program code, such as the MUT characterization system 218, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, the MUT characterization system 218 can be embodied as any combination of system software and/or application software. It is further understood that the MUT characterization system 218 can be implemented in a cloud-based computing environment, where one or more processes are performed at distinct computing devices (e.g., a plurality of computing devices 207), where one or more of those distinct computing devices may contain only some of the components shown and described with respect to the computing device 207 of FIG. 20.

Further, the MUT characterization system 218 can be implemented using a set of modules 232. In this case, a module 232 can enable the computer system 202 to perform a set of tasks used by the MUT characterization system 218, and can be separately developed and/or implemented apart from other portions of the MUT characterization system 218. As used herein, the term "component" means any configuration of hardware, with or without software, which implements the functionality described in conjunction therewith using any solution, while the term "module" means program code that enables the computer system 202 to implement the functionality described in conjunction therewith using any solution. When fixed in a storage component 206 of a computer system 202 that includes a processing component 104, a module is a substantial portion of a component that implements the functionality. Regardless, it is understood that two or more components, modules, and/or systems may share some/all of their respective hardware and/or software. Further, it is understood that some of the functionality discussed herein may not be implemented or additional functionality may be included as part of the computer system 202.

When the computer system 202 comprises multiple computing devices, each computing device may have only a portion of MUT characterization system 218 fixed thereon (e.g., one or more modules 232). However, it is understood that the computer system 202 and MUT characterization system 218 are only representative of various possible equivalent computer systems that may perform a process described herein. To this extent, in other embodiments, the functionality provided by the computer system 202 and MUT characterization system 218 can be at least partially implemented by one or more computing devices that include any combination of general and/or specific purpose hardware with or without program code. In each embodiment, the hardware and program code, if included, can be created using standard engineering and programming techniques, respectively.

Regardless, when the computer system 202 includes multiple computing devices, the computing devices can communicate over any type of communications link. Further, while performing a process described herein, the computer system 202 can communicate with one or more other computer systems using any type of communications link. In either case, the communications link can comprise any combination of various types of wired and/or wireless links; comprise any combination of one or more types of networks; and/or utilize any combination of various types of transmission techniques and protocols.

The computer system 202 can obtain or provide data, such as sensor data 160 and/or threshold data 162 using any solution. The computer system 202 can generate sensor data 260 and/or threshold data 262, from one or more data stores, receive sensor data 260 and/or threshold data 262, from another system such as the electrode array 200, signal generator/analyzer 203, user 212 and/or display 206, send sensor data 160 and/or threshold optical data 162 to another system, etc.

While shown and described herein as a method and system for characterizing an MUT (including, e.g., surface/subsurface), it is understood that aspects of the invention further provide various alternative embodiments. For example, in one embodiment, the invention provides a computer program fixed in at least one computer-readable medium, which when executed, enables a computer system to detect and characterize at least a portion of an MUT. To this extent, the computer-readable medium includes program code, such as the MUT characterization system 218 (FIG. 20), which implements some or all of the processes and/or embodiments described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; paper; etc.

In another embodiment, the invention provides a method of providing a copy of program code, such as the MUT characterization system 218 (FIG. 20), which implements some or all of a process described herein. In this case, a computer system can process a copy of program code that implements some or all of a process described herein to generate and transmit, for reception at a second, distinct location, a set of data signals that has one or more of its characteristics set and/or changed in such a manner as to encode a copy of the program code in the set of data signals. Similarly, an embodiment of the invention provides a method of acquiring a copy of program code that implements some or all of a process described herein, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the invention provides a method of generating a system for characterizing an MUT. In this case, a computer system, such as the computer system 202 (FIG. 20), can be obtained (e.g., created, maintained, made available, etc.) and one or more components for performing a process described herein can be obtained (e.g., created, purchased, used, modified, etc.) and deployed to the computer system. To this extent, the deployment can comprise one or more of: (1) installing program code on a computing device; (2) adding one or more computing and/or I/O devices to the computer system; (3) incorporating and/or modifying the computer system to enable it to perform a process described herein; etc.

In any case, the technical effect of the invention, including, e.g., the MUT characterization system 218, is to control operation of an electrode array 200, signal generator/analyzer 203, user 212 and/or display 206 to characterize at least a portion of an MUT in one of the various manners described and illustrated herein.

In various embodiments, components described as being "coupled" to one another can be joined along one or more interfaces. In some embodiments, these interfaces can include junctions between distinct components, and in other cases, these interfaces can include a solidly and/or integrally formed interconnection. That is, in some cases, components that are "coupled" to one another can be simultaneously formed to define a single continuous member. However, in other embodiments, these coupled components can be formed as separate members and be subsequently joined through known processes (e.g., fastening, ultrasonic welding, bonding).

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A system comprising:
    an array of electrodes for communicating with a surface and a subsurface beneath the surface;
    a signal generator operably connected with the array of electrodes; and
    at least one computing device operably connected with the signal generator and the array of electrodes, the at least one computing device configured to:
        instruct the signal generator to transmit a first set of tomographic signals from a first subset of the array of electrodes into the surface and the subsurface;
        obtain a first return signal from the array of electrodes after the transmitting of the first set of tomographic signals;
        instruct the signal generator to transmit a second set of tomographic signals from a second subset of the array of electrodes into the surface and the subsurface; based upon the first return signal, the second subset of the array of electrodes including at least one electrode not included in the first subset of the array of electrodes;
        obtain a second return signal from the array of electrodes after the transmitting of the second set of tomographic signals; and
        combine the first return signal and the second return signal to determine a characteristic of at least one of the surface or the subsurface.

2. The system of claim 1, wherein the array of electrodes includes a planar array of electrodes.

3. The system of claim 1, wherein a number of electrodes in the array of electrodes is equal to a number of combined layers, n, of the surface and the subsurface, plus one, n+1.

4. The system of claim 1, wherein a center-to-center spacing between adjacent electrodes in the array of electrodes is related to the minimum thickness of the layers of the surface and the subsurface to be measured.

5. The system of claim 1, wherein the array of electrodes includes a linear array of equally spaced electrodes configured to operate at a single frequency, and wherein the array of electrodes includes a single transmitting electrode positionally fixed in the linear array.

6. The system of claim 5, wherein the array of electrodes includes a plurality of linear sub-arrays of electrodes including an equal center to center spacing between adjacent electrodes within each sub-array, wherein a spacing between each sub-array of electrodes is at least as great as the spacing between the adjacent electrodes within each sub-array.

7. The system of claim 6, wherein the array of electrodes includes a planar array of electrodes including a plurality of linear sub-arrays of electrodes, wherein each of the plurality of sub-arrays of electrodes includes a single transmitting electrode positionally fixed in each sub-array.

8. The system of claim 7, wherein a center-to-center spacing between adjacent electrodes in each of the plurality of sub-arrays is equal to a minimum thickness of the layer to be detected in the subsurface, and wherein each of the plurality of sub-arrays is separated from an adjacent sub-array by a distance at least as great as the spacing between the adjacent electrodes.

9. The system of claim 7, wherein each of the plurality of sub-arrays is configured to operate at a distinct frequency from at least one of the other sub-arrays in the plurality of sub-arrays.

10. The system of claim 7, wherein the at least one computing device is configured to communicate with each of the plurality of sub-arrays based upon an area of detection in the subsurface.

11. A method of characterizing select volumes of a material under test (MUT) using an array of electrodes, the method comprising:
    instructing a signal generator to transmit a first set of tomographic signals from a first subset of the array of electrodes into the MUT;
    obtaining a first return signal from the array of electrodes after the transmitting of the first set of tomographic signals;
    instructing the signal generator to transmit a second set of tomographic signals from a second subset of the array of electrodes into the MUT based upon the first return signal, the second subset of the array of electrodes including at least one electrode not included in the first subset of the array of electrodes;
    obtaining a second return signal from the array of electrodes after the transmitting of the second set of tomographic signals; and
    combining the first return signal and the second return signal to determine a characteristic of the MUT.

12. The method of claim 11, further comprising providing instructions to select a number of electrodes in the first subset of the array of electrodes to operate and a number of electrodes in the second subset of the array of electrodes to operate based upon a number of layers in the MUT.

13. The method of claim 11, wherein the first return signal and the second return signal each include complex impedance data about at least one of a volume or a voxel of the MUT.

14. The method of claim 13, wherein the combining of the first return signal and the second return signal to determine a characteristic of the MUT includes applying at least one of a series or a parallel circuit approach to the complex impedance data based upon a location of the first subset of the array of electrodes and the second subset of the array of electrodes.

15. The method of claim 13, wherein the complex impedance data about the at least one of the volume or the voxel is correlated with physical properties of the MUT.

16. The method of claim 13, wherein the instructing of the signal generator to transmit the first set of tomographic signals, the obtaining of the first return signal, the instruction of the signal generator to transmit the second set of tomographic signals, and the obtaining of the second return signal are performed while the electrode array is in motion parallel to a plane co-planar with the array of electrodes, and wherein the first return signal and the second return signal are separated at a time interval, $\delta$.

17. A computer program product comprising program code stored on a non-transitory computer readable medium, which when executed by at least one computing device coupled to a signal generator and an array of electrodes, causes the at least one computing device to execute a method of characterizing select volumes of a material under test (MUT) by performing actions including:
    instructing the signal generator to transmit a first set of tomographic signals from a first subset of the array of electrodes into the MUT;
    obtaining a first return signal from the array of electrodes after the transmitting of the first set of tomographic signals;
    instructing the signal generator to transmit a second set of tomographic signals from a second subset of the array of electrodes into the MUT based upon the first return signal, the second subset of the array of electrodes including at least one electrode not included in the first subset of the array of electrodes;

obtaining a second return signal from the array of electrodes after the transmitting of the second set of tomographic signals; and combining the first return signal and the second return signals to determine a characteristic of the MUT.

18. The computer program product of claim 17, wherein the at least one computing device is further configured to provide instructions to select a number of electrodes in the first subset of the array of electrodes and a number of electrodes in the second subset of the array of electrodes based upon a number of layers in the MUT, wherein the selecting includes further selecting the number of electrodes in the first subset and the number of electrodes in the second subset based upon a center-to-center spacing between adjacent electrodes in the array of electrodes.

* * * * *